(12) United States Patent
Berelsman et al.

(10) Patent No.: US 7,625,406 B2
(45) Date of Patent: Dec. 1, 2009

(54) ELBOW PROSTHESIS

(75) Inventors: Brian K. Berelsman, Warsaw, IN (US);
Kevin T. Stone, Winona Lake, IN (US);
Thomas J. Graham, Lutherville, MD
(US); Hill Hastins, Zionsville, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 0 days.

(21) Appl. No.: 11/780,365

(22) Filed: Jul. 19, 2007

(65) Prior Publication Data

US 2008/0033566 A1 Feb. 7, 2008

Related U.S. Application Data

(62) Division of application No. 10/333,140, filed as application No. PCT/US01/22338 on Jul. 17, 2001, now Pat. No. 7,247,170.

(60) Provisional application No. 60/219,103, filed on Jul. 18, 2000.

(51) Int. Cl.
*A61F 2/30* (2006.01)

(52) U.S. Cl. ............... 623/18.11; 623/20.11; 623/20.12; 623/23.39

(58) Field of Classification Search ............... 623/20.12, 623/20.13, 20.25, 20.26
See application file for complete search history.

(56) References Cited

U.S. PATENT DOCUMENTS

| | | | |
|---|---|---|---|
| 3,694,821 A | 10/1972 | Moritz | |
| 3,708,805 A | 1/1973 | Scales et al. | |
| 3,816,854 A | 6/1974 | Schlein | |
| 3,824,630 A | 7/1974 | Johnston | |

(Continued)

FOREIGN PATENT DOCUMENTS

DE 2806717 8/1979

(Continued)

OTHER PUBLICATIONS

DePuy Orthopaedics, Inc., web page print out—http://www/allaboutarthritis.com/AllAbout Arthritis/layoutTemplates/html/en/contentdisplay/document/condition/arthritis/clinicalArticle/Elbow_Replacement_Surgery.htm, 2000-2005—printed Dec. 14, 2005.

(Continued)

*Primary Examiner*—Bruce E Snow
*Assistant Examiner*—Melissa Montano
(74) *Attorney, Agent, or Firm*—Harness, Dickey

(57) ABSTRACT

A prosthetic joint kit, particularly well suited for an elbow, transmits load through the prosthetic joint through a pair of spherically shaped bearing surfaces so as to transmit load over a relatively large area rather than at a point or over a line of contact. The prosthetic joint kit may be configured in a modular manner wherein a plurality of interchangeable stem structures, bearing structures and/or bearing inserts of various types are available. Construction in this manner enables a surgeon to configure the prosthetic joint to best suit the needs of the patient. For example, the surgeon may employ a modular flange for compressing a bone graft, a tissue fastener for securing soft tissue to a portion of the prosthetic joint, a cam for limiting the amount by which the prosthetic joint articulates or a bearing insert for tailoring the degree of varus/valgus constraint.

14 Claims, 19 Drawing Sheets

U.S. PATENT DOCUMENTS

| | | | |
|---|---|---|---|
| 3,852,831 A | | 12/1974 | Dee et al. |
| 3,939,496 A | | 2/1976 | Ling et al. |
| 3,946,445 A | | 3/1976 | Bentley et al. |
| 3,990,117 A | * | 11/1976 | Pritchard et al. ......... 623/20.12 |
| 4,008,495 A | | 2/1977 | Cavendish et al. |
| 4,038,704 A | | 8/1977 | Ring et al. |
| 4,079,469 A | | 3/1978 | Wadsworth et al. |
| 4,129,902 A | * | 12/1978 | Harmon ................... 623/20.12 |
| 4,131,956 A | | 1/1979 | Treace |
| 4,131,957 A | | 1/1979 | Bokros |
| 4,194,250 A | | 3/1980 | Walker |
| 4,224,695 A | | 9/1980 | Grundei et al. |
| 4,224,697 A | * | 9/1980 | Murray et al. ........... 623/20.25 |
| 4,242,758 A | | 1/1981 | Amis et al. |
| 4,280,231 A | | 7/1981 | Swanson |
| 4,293,963 A | | 10/1981 | Gold et al. |
| 4,301,552 A | * | 11/1981 | London ................... 623/20.13 |
| 4,378,607 A | | 4/1983 | Wadsworth et al. |
| 4,383,337 A | * | 5/1983 | Volz et al. ................ 623/20.12 |
| 4,538,306 A | | 9/1985 | Dorre et al. |
| 4,725,280 A | | 2/1988 | Laure |
| 4,759,768 A | | 7/1988 | Hermann et al. |
| 4,822,364 A | | 4/1989 | Inglis et al. |
| 4,911,719 A | | 3/1990 | Merle et al. |
| 5,282,867 A | | 2/1994 | Mikhail |
| 5,376,121 A | * | 12/1994 | Huene et al. ............. 623/20.12 |
| 5,411,555 A | | 5/1995 | Nieder |
| 5,702,471 A | | 12/1997 | Grundei et al. |
| 5,725,541 A | | 3/1998 | Anspach, III et al. |
| 5,782,923 A | | 7/1998 | Engelbrecht et al. |
| 5,879,395 A | | 3/1999 | Tornier et al. |
| 6,027,534 A | * | 2/2000 | Wack et al. .............. 623/20.12 |
| 6,120,543 A | | 9/2000 | Kubein-Meesenburg et al. |
| 6,290,725 B1 | | 9/2001 | Weiss et al. |
| 6,379,387 B1 | | 4/2002 | Tornier et al. |
| 6,767,368 B2 | | 7/2004 | Tornier et al. |
| 6,890,357 B2 | * | 5/2005 | Tornier ................... 623/20.12 |
| 2004/0243243 A1 | * | 12/2004 | Tornier ................... 623/20.12 |

FOREIGN PATENT DOCUMENTS

| | | |
|---|---|---|
| FR | 2634373 | 1/1990 |
| GB | 1520162 | 8/1978 |
| SU | 1560183 A | 7/1988 |
| SU | 1567200 A | 5/1990 |

OTHER PUBLICATIONS

Discovery Elbow System brochure, Surgical Technique, Biomet Orthopedics, Inc., © 2002.

International Search Report for PCT/US01/22338 mailed Jan. 3, 2002 based on U.S. Appl. No. 60/219,103, filed Jul. 18, 2000.

Joint Replacement, Overview, © DePuy Orthopedics, Inc., www.jointreplacement.com/xq/ASP.default/mn.local/pg.list/joint__id.2/list__id.59/newFont.2/joint__nm.Elbow/local__id.18/qx/default.htm, 2000-2005.

Joint Replacement, Surgery, © DePuy Orthopaedics, Inc., www.jointreplacement.com/xq/ASP.default/mn.local/pg.list/joint__id.2/list__id.59/newFont.2/joint__nm.Elbow/local__id.18/qx/default.htm, 2000-2005.

Latitude®, "Total Elbow Prosthesis, A new generation is born naturally precise", Tornier [undated].

Latitude®, "Total Elbow Prosthesis, Surgical Technique", Tornier pp. 1-39 [undated].

* cited by examiner

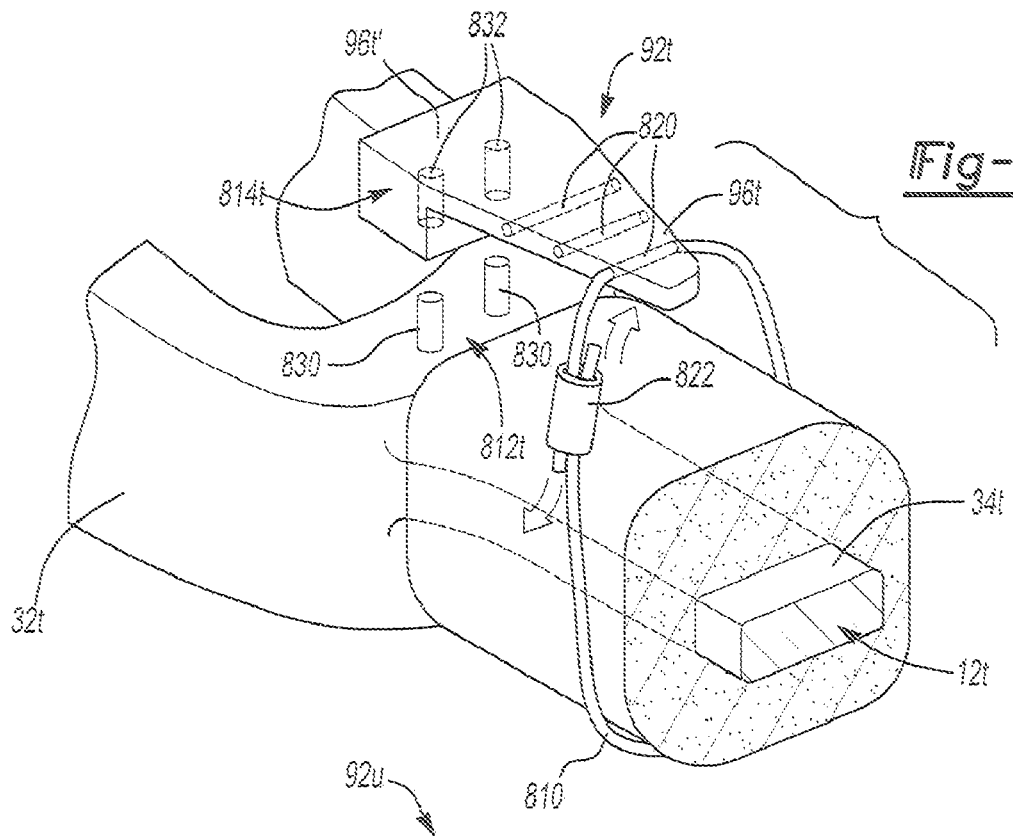
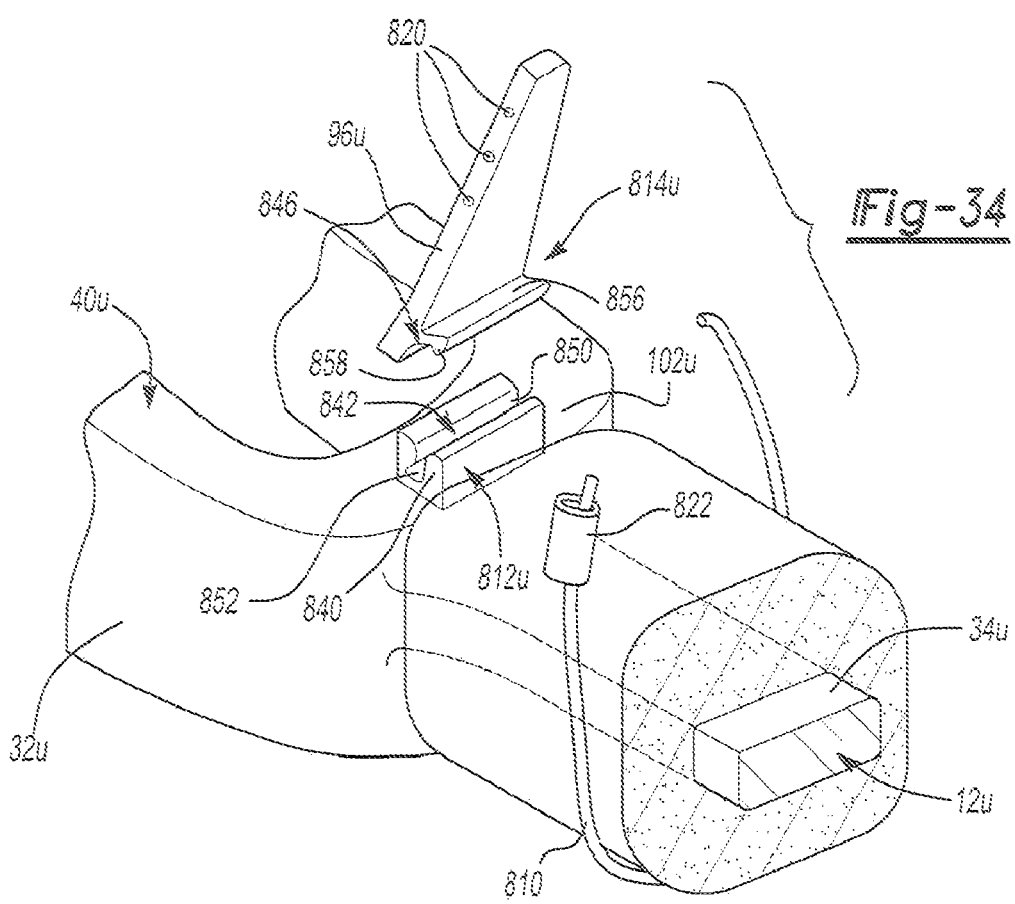

ELBOW PROSTHESIS

CROSS-REFERENCE TO RELATED APPLICATIONS

This application is a divisional of U.S. patent application Ser. No. 10/333,140 filed on Jan. 15, 2003, now U.S. Pat. No. 7,247,170, which is a National Stage of International Application No. PCT/US01/22338, filed Jul. 17, 2001, which claims benefit of U.S. Provisional Application No. 60/219,103, filed on Jul. 18, 2000. The disclosure(s) of the above application(s) is (are) incorporated herein by reference.

BACKGROUND OF THE INVENTION

1. Technical Field

The present invention relates generally to prosthetic devices used in elbow arthroplasty and more particularly to a modular elbow prosthesis.

2. Background Art

Linked or constrained elbow prosthesis are known which comprise simple hinge arrangements, one component of which is attached to the end of the humerus and the other component of which is attached to the end of the ulna. The humeral component includes a shaft that is cemented into a prepared cavity in the end of the humerus, and the ulnar component includes a shaft, that is cemented to end of the ulna. The components of the prosthesis are connected together by means of a hinge pin so that the prosthesis allows a single degree of freedom of movement of the ulna relative to the humerus.

One example of a link elbow prostheses is disclosed in U.S. Pat. No. 6,027,534 to Wack et al. In several respects, the linked embodiment of the '534 patent is typical of the designs for linked elbow prostheses in that it includes a humeral stem that terminates at a yoke at its distal end, a bearing component, retaining pin and an ulna stem. The bearing component includes an oversized hole that is aligned with the longitudinal axis of the bearing and adapted to accept the retaining pin in a slip-fit condition. The distal end of the bearing component is coupled to the ulna stem. Despite the relatively widespread use of the designs of the type, several drawbacks have been noted.

One significant drawback concerns the assembly of the elbow prosthesis after the surgeon has cemented the humeral and ulna stems to their respective bones. In using such conventionally configured linked elbow prosthesis devices, it is frequently necessary for the surgeon to drill a fairly large hole through the humerus so that the retaining pin may be inserted to the yoke of the humeral stem and the humeral bearing component. As a high degree of accuracy is typically required to ensure proper alignment between the hole in the humerus and the hole in the yoke of the humeral stem, a significant cost can be associated with this step in the installation of an elbow prosthesis due to the cost of the tooling used and the amount of amount of time required to complete this step. The other method for attaching the prosthetic device includes inserting the device in its linked condition or placing the remaining piece into the yoke prior to fully seating the humeral component into the bone. This later method is typically somewhat difficult, given the limited amount of joint space that is available and the time constraints associated with a use of a PMMA bone cement.

Unlinked, or unconstrained, elbow prostheses are known which are similar to linked elbow prostheses but do not have a specific component which mechanically couples the humeral and ulnar stems together. Rather, prosthetic device is held together by the patient's natural soft tissues. One example of an unlinked elbow prostheses is also disclosed in U.S. Pat. No. 6,027,534 to Wack et al. In several respects, the unlinked embodiment of the '534 patent is similar to the linked embodiment discussed above in that it includes a humeral stem that terminates at a yoke at its distal end, a humeral bearing component, a retaining pin, an ulnar bearing component and a ulnar stem. The outer surface of the humeral bearing is contoured to match the contour of the ulnar bearing component. Despite the relativity widespread use of designs of this type, several drawbacks have been noted.

For instance, a retaining pin that is transverse to the longitudinal axis of the patient is employed, thereby making its removal difficult if a bearing need to be replaced.

SUMMARY OF THE INVENTION

It is general object of the present invention to provide a prosthetic joint kit which transmits load through mating bearing components over a spherically shaped area so as to minimize stresses in the bearing components, more accurately mimic normal joint motion and provide for ease of assembly and revision.

In one preferred form, the present invention provides a prosthetic joint kit having a first bearing component and a second bearing component. The first bearing component includes a pair of condyle portions, each of which having a spherically shaped bearing portion. The second bearing component includes a pair of spherical bearing portions which are configured to engage the spherically shaped bearing portions of the first bearing component.

It is another general object of the present invention to provide a prosthetic joint kit having a high degree of plurality to permit a surgeon to easily configure the prosthetic joint kit to a patient.

In another preferred form, the present invention provides a prosthetic joint kit having a plurality of modular and interchangeable joint components which permit a surgeon to easily configure the prosthetic joint kit to a patient. Modularity is achieved through a plurality of interchangeable components such as stem structures, bearing components and bearing inserts.

It is yet another general object of the present invention to provide a prosthetic joint kit having a plurality of interchangeable bearing inserts which permit a surgeon to tailor the degree of varus/valgus constraint in a desired manner.

In another preferred form, the present invention provides a prosthetic joint kit having a plurality of interchangeable bearing inserts, each of which having a pair spherical depressions. Each of the spherical depressions has a first portion and a second portion, with the second portion being formed in a manner that defines the degree of varus/valgus constraint. It is a further of the present invention to provide a prosthetic joint kit which effectively limits the amount by which the prosthetic joint will articulate.

In yet another preferred form, the present invention provides a prosthetic joint kit having a cam structure which is coupled to a first stem structure such that the first stem structure contacts a second stem when first stem structure has been rotated to a predetermined position relative to the second stem structure.

It is yet another object of the present invention to provide a prosthetic joint kit which employs a spherically-shaped bearing surface to transmit load between stem structures yet does not require fasteners or other hardware to link the stem structures together.

In another preferred form, the present invention provides a prosthetic joint kit having a first stem structure with a retaining structure and a first spherical bearing surface and a second stem structure with a retaining aperture and a second spherical bearing surface. The retaining aperture is configured to receive the retaining structure when the first stem structure is at a first orientation relative to the second stem structure. Relative rotation of the first stem structure from the first orientation causes retaining structure to engage a portion of the retaining aperture which preludes the withdrawal of the retaining structure therefrom. The retaining aperture and retaining structure are sized so as not transmit load therebetween, thereby ensuring that load is transmitted between the spherical bearing surfaces of the first and second stem structures.

BRIEF DESCRIPTION OF THE DRAWINGS

Additional advantages and features of the present invention will become apparent from subsequent description and the appended claims, taken in conjunction with the accompanying drawings, wherein.

FIG. 33 is a view similar to that of FIG. 31 but illustrating a second alternative coupling means;

FIG. 34 is a view similar to that of FIG. 31 but illustrating a third alternative coupling means;

DETAILED DESCRIPTION OF THE PREFERRED EMBODIMENT

Figure 1:
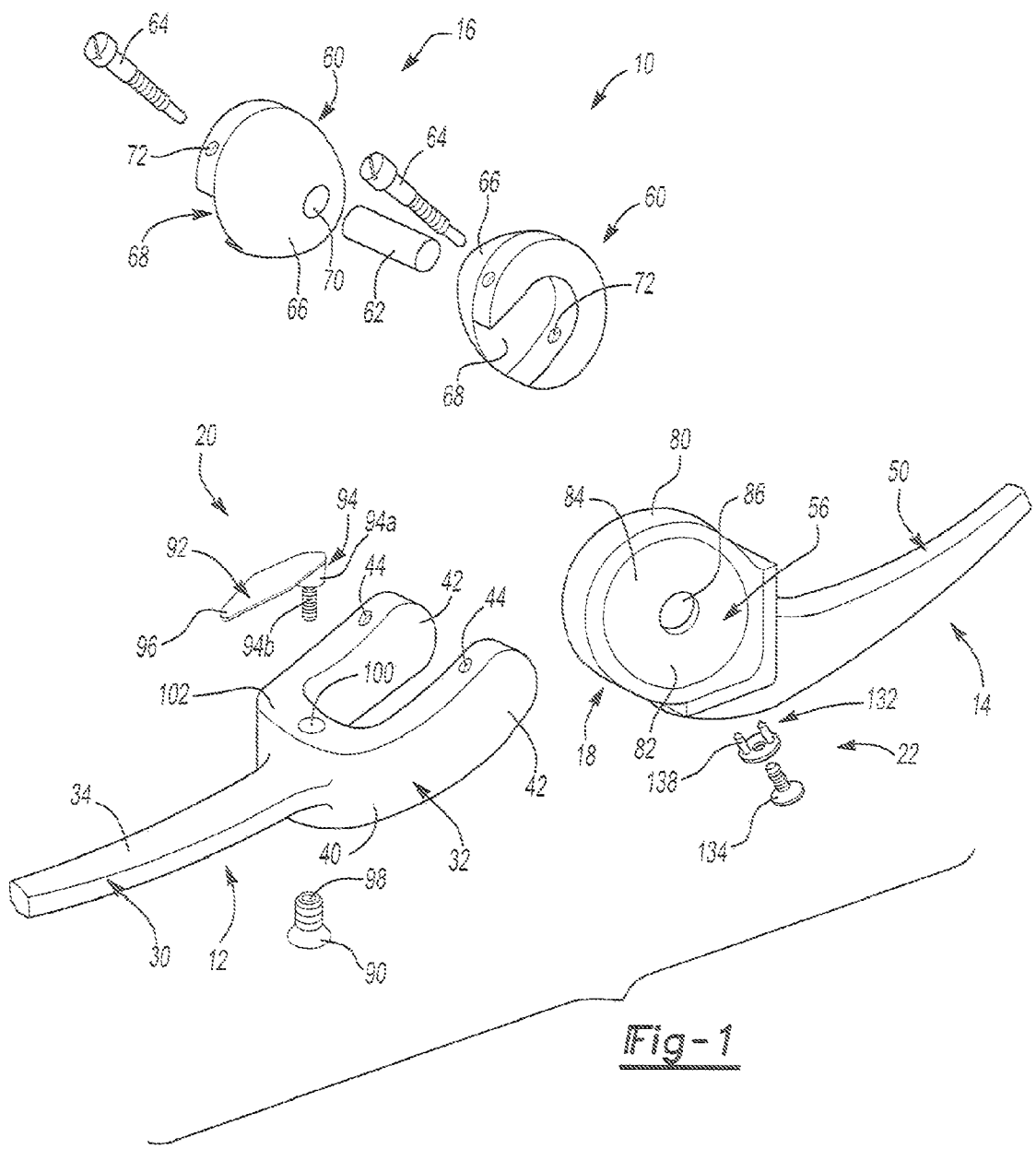
FIG. 1 is an exploded perspective view of a linked prosthetic joint kit constructed in accordance with the teachings of a first aspect of the present invention.
Figure 2:
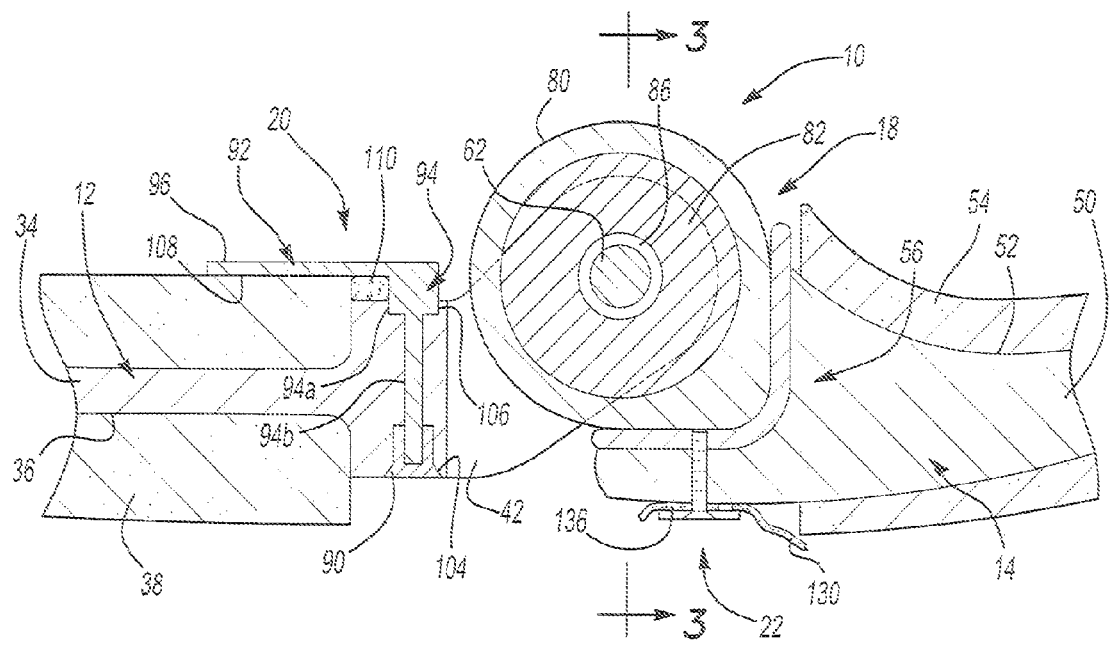
FIG. 2 is a longitudinal cross-sectional view of the linked prosthetic joint kit of FIG. 1 implanted in the arm of a person.
Figure 3:
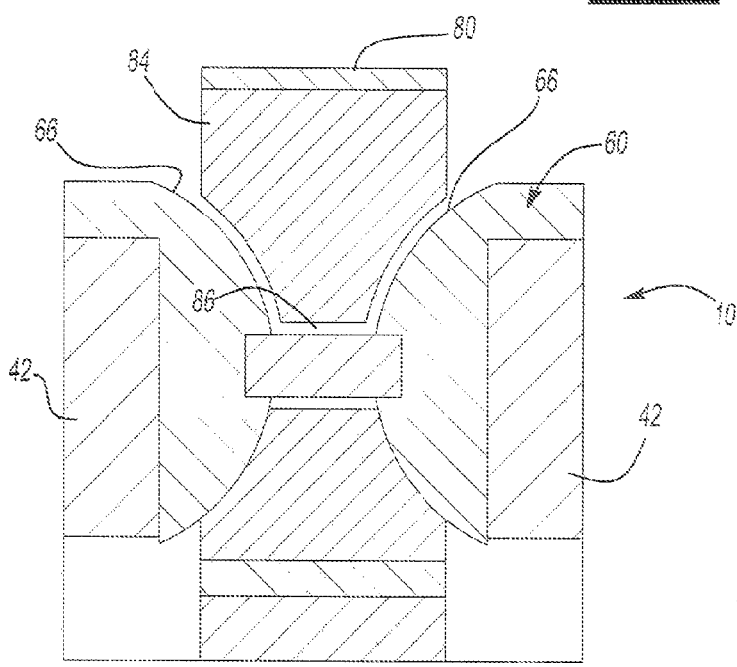
FIG. 3 is a cross-sectional view taken along the line 3-3 of FIG. 2.

With reference to FIGS. 1, 2 and 3 of the drawings, a linked prosthetic joint device constructed in accordance with the teachings of a first aspect of the present invention is generally indicted by reference number 10. Although the particular prosthesis illustrated and discussed relates to a prosthesis for use in reconstructing an elbow, it will be understood that the teachings of the present invention have applicability to other types of linked and unlinked prosthetic devices. As such, the scope of the present invention will be limited to applications involving elbow prosthesis but will extend to other prosthetic applications.

In the particular embodiment illustrated, linked prosthetic joint 10 is shown to include a first stem structure 12, a second stem structure 14, a first bearing component 16, a second bearing component 18, a modular flange 20 and a tissue fastener 22. First stem structure 12 includes a proximal portion 30 and a distal portion 32. Proximal portion 30 includes a stem member 34 which is adapted to fit within the medullary canal 36 of a humerus 38. Distal portion 32 includes a generally U-shaped member 40 which is fixedly coupled to the distal end of proximal portion 30. U-shaped portion 40 includes a pair of spaced-apart legs or furcations 42. A threaded fastener aperture 44 extends perpendicularly through each of the furcations 42.

Second stem structure 14 includes a distal portion 50 which is adapted to fit within the medullary canal 52 of an ulna 54. Second stem structure 14 also includes a proximal portion 56 which is coupled to second bearing component 18. In the particular embodiment illustrated, second bearing component 18 is fixedly coupled to second stem structure 14. However, second bearing component 18 may also be releasably coupled to second stem structure 14 as shown in FIGS. 9 through 12.

First bearing component 16 includes a pair of condyle portions 60, a pin portion 62 and a pair of fasteners 64. Condyle portions 60 and pin portion 62 are formed from a suitable material, such as cobalt chromium alloy. Each condyle portion 60 is shown to include spherically-shaped bearing portion 66, slotted aperture 68, a pin aperture 70 and a mounting aperture 72. The pair of spherically shaped bearing portions 66 collectively form a first bearing surface. Pin aperture 70 is sized to receive an end of pin portion 62 to permit pin portion 62 to slidingly engage condyle portions 60. Pin 62 can also be fixedly coupled with one of said condyle portion 60 and slidingly engage second of said condyle portion 60. Each of the slotted apertures 68 is sized to slidingly engage one of the furcations 42.

Second bearing component 18 is shown to include a cage portion 80 which is fixedly coupled to the proximal portion 56 of second stem structure 14 and a bearing member 82 which is fixedly coupled to the cage portion 80. Bearing member 82 includes a pair of spherical bearing portions 84 which are configured to engage the spherically shaped bearing portions 66 of the condyle portions 60. The pair of spherical bearing surfaces 84 collectively form a second bearing surface that mates with the first bearing surface. Bearing member 82 also includes a through hole 86 which is adapted to receive pin portion 62, preferably without transmitting load therebetween (i.e., pin portion 62 preferably does not contact the surfaces of through hole 86). In the particular embodiment illustrated, bearing member 82 is fabricated form polyethylene which has been molded to cage portion 80. Alternatively, bearing member 82 may be fabricated from any other appropriate material such as a stainless steel, ceramic, pyrolytic carbon, cobalt chrome (CoCr) etc.

To use linked prosthetic joint 10, first stem structure 12 is implanted in humerus 38 such that proximal portion 34 is located in the medullary canal 36 of the humerus 38 as shown in FIG. 2. Second stem structure 14 is similarly implanted in ulna 54 such that distal portion 50 is located in the medullary canal 52. Pin portion 62 is next inserted to the pin aperture 70 of one of the condyle portions 60 and the opposite end of pin portion 62 is place through hole 86 and into the pin aperture 70 of the other one of the condyle portions 60. Second bearing component 18 is positioned adjacent the distal portion 32 of first stem structure 12, furcations 42 are aligned to their respective slotted aperture 68 and condyle portions 60 are slidingly engaged to furcations 42. Fasteners 64 are inserted through their respective mounting apertures 72 and threadably engaged to their threaded fastener aperture 44. When fully seated, each of the fasteners 72, extends through its respective furcation 42 to prevent condyle portion 60 from rotating relative to the furcation 42. At this point, first and second bearing components 16 and 18 hingedly couple first and second stem structures 12 and 14 together in a linked or constrained manner.

Construction of linked prosthetic joint 10 in this manner is highly advantageous in that it permits the surgeon to insert the first and second stem structures 12 and 14 prior to or after assembling linked prosthetic joint 10, as well as permits linked prosthetic joint 10 to be assembled in a relatively small space as compared to most of the other prosthetic joints that are known in the art. Furthermore, the spherical configuration of first and second bearing surfaces 66 and 84 permits the load which is transmitted through linked prosthetic joint 10 to be spread out over a relatively large area, rather than concentrated at a single point or over a line of contact to thereby improve the durability of linked prosthetic joint 10.

Modular flange 20 may be employed to increase the resistance of first stem structure 12 to rotation within medullary canal 36. In FIGS. 1 and 2, modular flange 20 is shown to include an internally threaded fastener 90, and a unitarily formed flange structure 92 having a mount member 94 and a flange member 96. Mount member 94 includes a locating cylinder 94a which is fixedly coupled to flange member 96 at its base and an externally threaded fastener 94b which is coupled to an opposite side of locating cylinder 94a. A mounting hole 98, which is sized to receive fastener 94b, extends through internally threaded fastener 90. A bore 100 formed through the base 102 of U-shaped portion 40 has a first portion 104 which is tapered at one end to engage the edges of internally threaded fastener 90 and a second portion 106 which is counter bored at the other end to engage the locating cylinder 94a of mount member 94. Internally threaded fastener 90 is threadably engaged to fastener 94b to fixedly but removably couple modular flange 20 to first stem structure 12.

Modular flange 20 may be employed to generate a clamping force which clamps a portion 108 of the humerus 38 between the proximal portion 34 of the first stem structure 12 and the flange member 96. Preferably, a bone graft 110 is employed in conjunction with modular flange 20 such that the clamping force produced by modular flange 20 is also transmitted to bone graft 110 to promote the attachment of bone graft 110 to humerus 38 and the subsequent growth of bone graft 110. Those skilled in the art will understand that alternatively, a flange (not shown) which is unitarily formed with first stem structure 12 may be incorporated into linked prosthetic joint 10 to thereby increase the resistance of first stem structure 12 to rotation within medullary canal 36. However, a flange which is unitarily formed with first stem structure 12 could not be employed to generate a clamping force which clamps portion 108 of the humerus 38 between the proximal portion 34 of the first stem structure 12 and the flange.

Tissue fastener 22 is shown in FIGS. 1 and 2 to be a device for attaching soft tissue, such as tendons 130, to linked prosthetic joint 10. In this regard, the specific configuration of tissue fastener is beyond the scope of this disclosure. Examples of suitable tissue fasteners are discussed in U.S. Pat. Nos. 5,380,334, 5,584,835, 5,725,541, 5,840,078 and 5,980,557 which are hereby incorporated by reference as if fully set forth herein.

In the particular embodiment illustrated, tissue fastener 22 is shown to include a tissue clamp 132 and a threaded fastener 134. Tissue clamp 132 includes an annular base 136 and a pair of prongs 138. Prongs 138 are forced through the soft tissue (e.g. tendons 130). Threaded fastener 134 is inserted through a hole in base 136 and threadably engaged to second stem structure 14 to fixedly but releasably couple tissue fastener 22 and the soft tissue to second stem structure 14. Those skilled in the art will understand that tissue fastener 22 may also be used in conjunction with first stem structure 12.

Figure 1A:
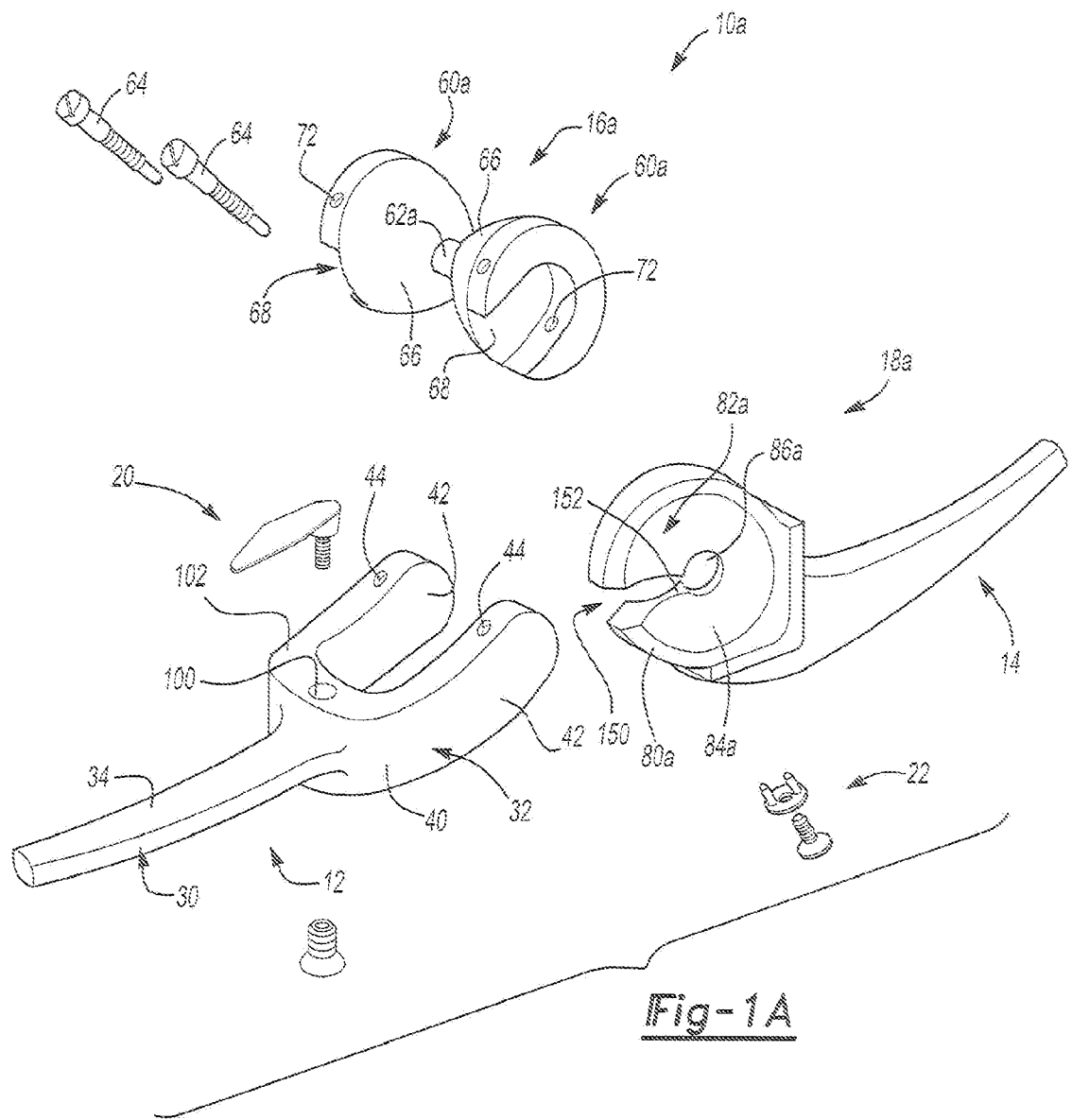
FIG. 1A is an exploded perspective view of a linked prosthetic joint kit similar to that of FIG. 1 but constructed in accordance with first alternate embodiment of the aspect of the present invention.

In FIG. 1A, a linked prosthetic joint device constructed in accordance with the teachings of an alternate embodiment of the first aspect of the present invention is generally indicated by reference numeral 10a. Linked prosthetic joint 10a is shown to include first stem structure 12, second stem structure 14, first bearing component 16a, second bearing component 18a, modular flange 20 and tissue fastener 22.

First bearing component 16a is similar to first bearing component 16 in all respects except that it is unitarily formed. Accordingly, pin portion 62a is not removable form condyle portions 60a. Second bearing component 18a is similar to second bearing component 18 in all respects except that an insertion aperture 150 extends form through hole 86a outwardly through bearing member 82a and cage portion 80a. Accordingly, insertion aperture 150 renders the area of second bearing surface 84a somewhat smaller than second bearing surface 84. Second bearing surface 84a is otherwise identical to second bearing surface 84.

To use linked prosthetic joint device 10a, first and second stem structures 12 and 14 are initially inserted to the humerus and ulna and first bearing component 16a is fastened to the first stem structure 12 using techniques similar to that discussed above for prosthetic joint device 10. First bearing component 16a is then positioned adjacent second bearing component 18a such that pin portion 62a is in insertion aperture 150. Pin portion 62a is then forced toward through hole 86a. The distal end 152 of insertion aperture 150 is smaller than pin portion 62a to permit bearing member 82a to engage pin portion 62a in a snap fit manner, so as to inhibit the unintentional withdrawal of pin portion 62a from through hole 86a. As discussed above, through hole 86a is preferably larger in diameter than pin portion 62a. At this point, first and second bearing components 16a and 18a hingedly couple first and second stem structures 12 and 14 together in a linked manner.

Figure 4:
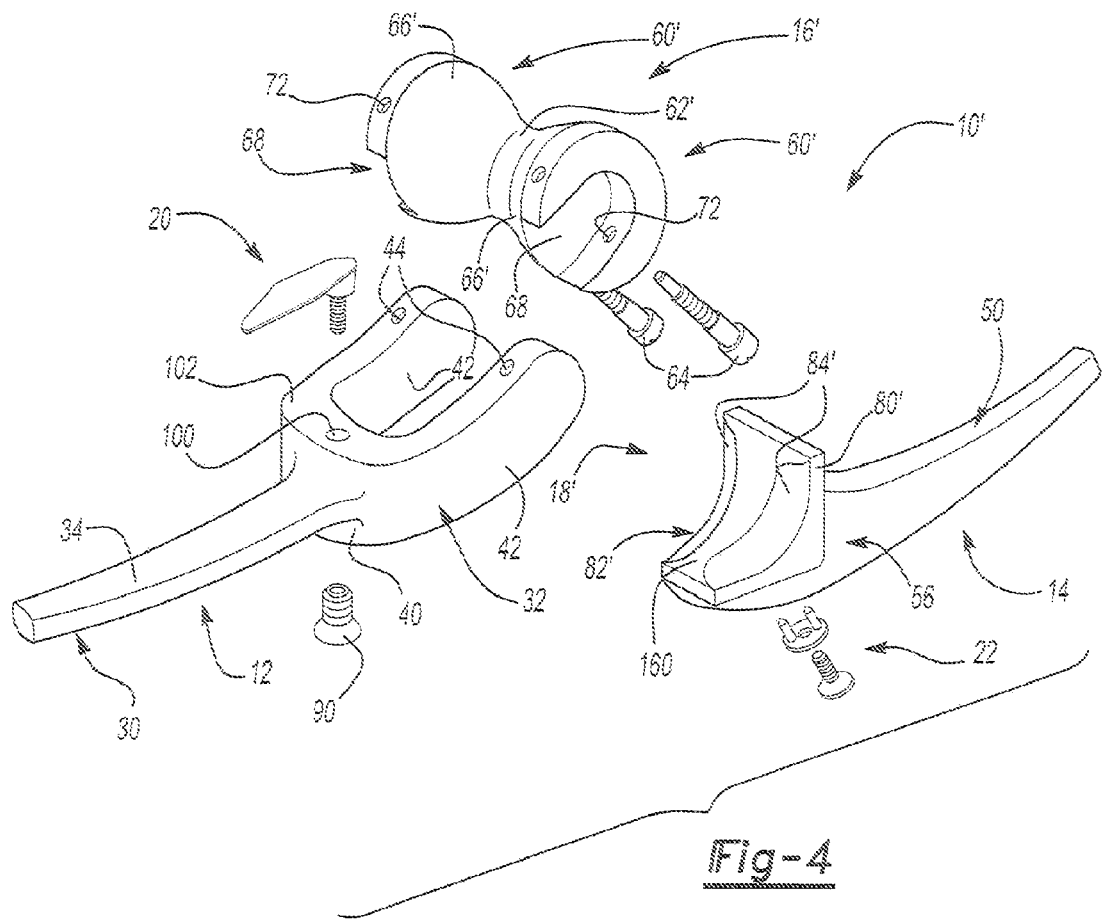
FIG. 4 is an exploded perspective view of an unlinked prosthetic joint constructed in accordance with the teachings of a first aspect of the present invention.
Figure 5:
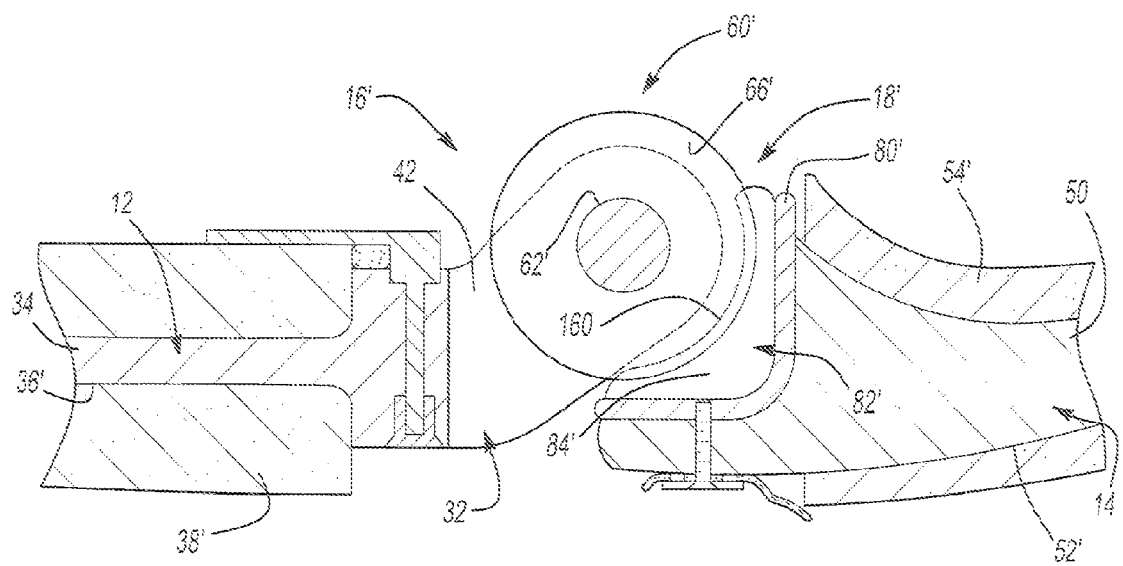
FIG. 5 is a longitudinal cross-sectional view of the unlinked prosthetic joint kit of FIG. 4 implanted in the arm of a person.

In FIGS. 4 and 5, an unconstrained or unlinked prosthetic joint device constructed according to a first aspect of the present invention is generally indicated by reference number 10'. Unlinked prosthetic joint 10' is shown to include a first stem structure 12, a second stem structure 14, a first bearing component 16', a second bearing component 18', a modular flange 20 and a tissue fastener 22. Unlinked prosthetic joint 10' is shown to be operatively associated with a humerus 38' and an ulna 54' (FIG. 5), but those skilled in the art will understand that the teachings of the present invention have application to prosthetic joints for other applications and as such, the scope of the present invention will not be limited to elbow joints.

First bearing component 16' is similar to first bearing component 16 in that it includes a pair of condyle portions 60' and a pin portion 62'. However, first bearing component 16' is preferably unitarily formed with pin portion 62' extending between the spherically-shaped bearing portions 66' and fixedly coupling the spherically-shaped bearing portions 66' thereto. Like first bearing component 16, each of the condyle portions 60' of first bearing component 16' includes a slotted aperture 68 and a fastener aperture 72. Spherically shaped bearing portions 66' collectively form a first bearing surface. Like first bearing component 16, first bearing component 16' may be made from any appropriate bearing material, such as cobalt chromium alloy.

Second bearing component 18' is similar to second bearing component 18 in that is includes a cage portion 80' which is fixedly coupled to the proximal portion 56 of second stem structure 14 and a bearing member 82' which is fixedly coupled to the cage portions 80'. For purposed of clarity, bearing member 82' has not been shown in cross section in FIG. 5. Bearing member 82' includes spherical bearing surfaces 84' which are adapted to engage the spherically-shaped bearing portions 66' of the condyle portions 60'. The pair of bearing surfaces 84' collectively form a second bearing surface that mates with the first bearing surface. Bearing member 82' also includes a raised portion 160 which is adjacent the spherical bearing surfaces 84' and configured to clear pin portion 62', preferably without transmitting load therebetween (i.e., pin portion 62' preferably does not contact the surfaces of raised portion 160). In the particular embodiment illustrated, bearing member 82' is fabricated from polyethylene which has been molded to cage portion 80. Alternatively, bearing member 82' may be fabricated from any other appropriate material such as a cobalt chromium alloy, ceramics, or stainless steel.

To use unlinked prosthetic joint 10', first stem structure 12 is implanted in humerus 38' such that proximal portion 34 is located in the medullary canal 36' as shown in FIG. 5. Second stem structure 14 is similarly implanted in ulna 54' such that distal portion 50 is located in the medullary canal 52'. First bearing component 16' is next positioned adjacent the distal portion 32 of first stem structure 12 and furcations 42 are engaged to slotted apertures 68. Fasteners 64 are inserted through their respective mounting apertures 72 and threadably engaged to their threaded fastener aperture 44. When fully seated, each of the fasteners 64, extends through its respective furcation 42 to prevent its associated condyle portion 60' from rotating relative to thereto. The proximal end of the ulna 54' is positioned adjacent the distal end of the humerus 38' such that the pin portion 62' is proximate the raised portion 160 and the spherically-shaped bearing portions 66' of the condyle portions 60' engage the spherical bearing surface 84'. At this point, first and second bearing components 16' and 18' are coupled together in an unconstrained or unlinked manner (i.e., held in position by the soft tissues of the elbow). Construction of unlinked prosthetic joint 10' in this manner provides many of the same advantages as mentioned above for linked prosthetic joint 10, such as the ability of first and second bearing surfaces 16' and 18' to spread out the load that is transmitted through unlinked prosthetic joint 10' over a relatively large area, rather than concentrate the load at a single point or over a line of contact to thereby improve the durability of unlinked prosthetic joint 10'.

As a surgeon may not always know prior to beginning an operation whether a patient would be better served by a linked or an unlinked joint prosthesis and as it is also occasionally necessary to convert an unlinked joint prosthesis to a constrained joint prosthesis, or vice versa, after implementation and use for a period of time, it is highly desirable that the joint prosthesis be modular so as to provide the surgeon with a high degree of flexibility which may be achieved in a relatively simple and cost-effective manner.

Figure 6:
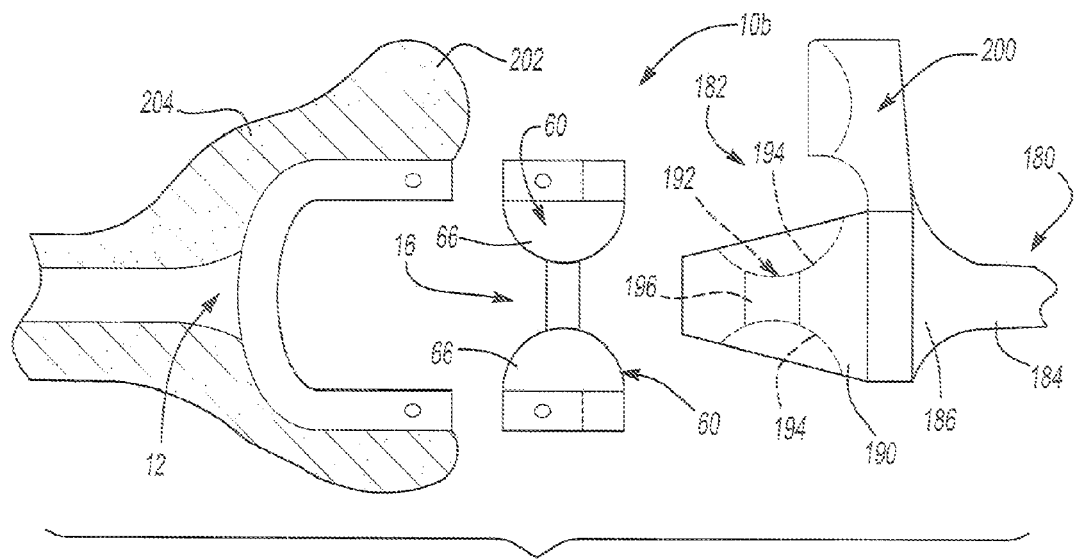
FIG. 6 is an exploded plan view of a linked prosthetic joint kit constructed in accordance with a second alternate embodiment of the first aspect of the present invention.
Figure 7:
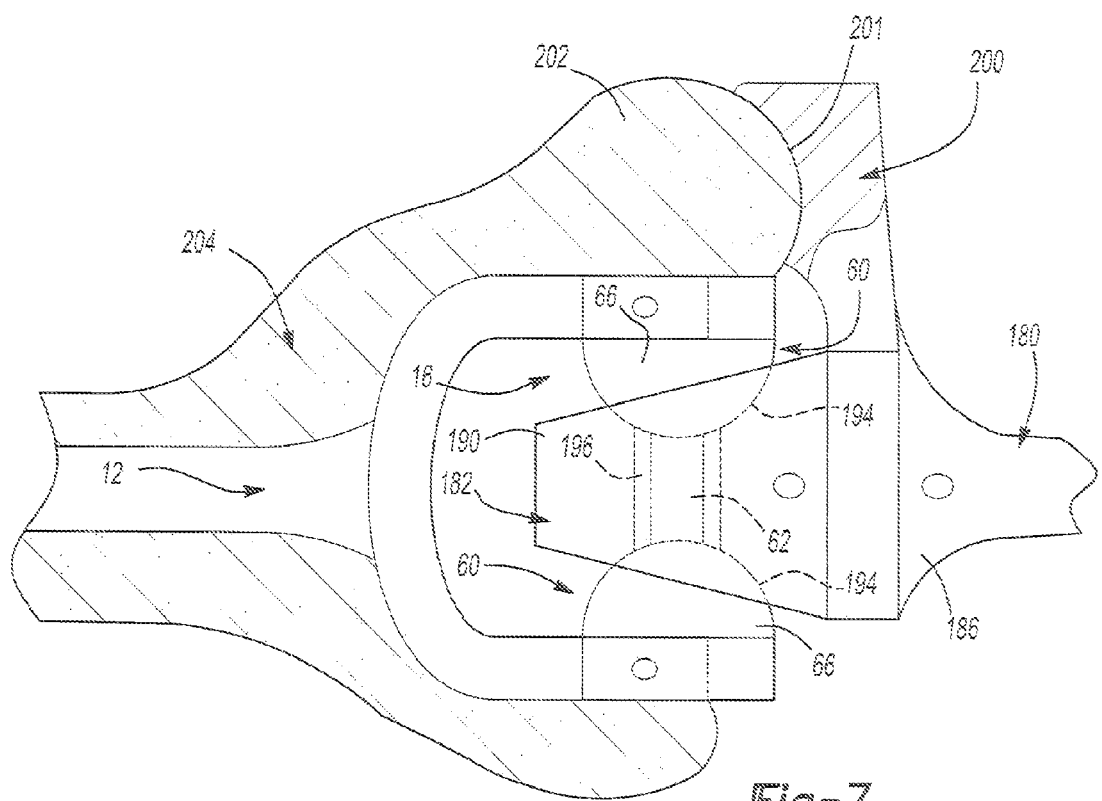
FIG. 7 is an enlarged portion of the linked prosthetic joint kit of FIG. 6.

In FIGS. 6 and 7, a linked prosthetic joint constructed in accordance with a second aspect of the present invention is generally indicated by reference numeral 10b. Linked prosthetic joint 10b is shown to include first stem structure 12, a third stem structure 180, first bearing component 16, a third bearing component 182. Third stem structure 180 is similar to second stem structure 14 in that it includes a distal portion 184 which is adapted to fit within the medullary canal of an ulna. The proximal portion 186 of third stem structure 180 is coupled to third bearing component 182.

Third bearing component 182 is similar to second bearing component 18 in that it includes a cage portion 190 and a bearing member 192. Cage portion 190 is fixedly coupled to the proximal portion 186 of third stem structure 180. Bearing member 192 is fixedly coupled to cage portion 190. Bearing member 192 includes a pair of spherical bearing surfaces 194 which are configured to engage the spherically-shaped bearing portions 66 of the condyle portions 60 and a through hole 196 which is configured to receive pin portion 62, preferably without transmitting load therebetween (i.e., pin portion 62 preferably does not contact the surfaces of through hole 196). Bearing member 182 also includes a lateral buttress 200. Lateral buttress 200 includes a supplementary bearing surface 201 which is configured for receiving a capitellum 202 of the humerus 204. In the particular embodiment illustrated, third bearing component 182 is fixedly coupled to third stem structure 180 and as such, the combination of the second stem structure 14 and second bearing component 18 is interchangeable with the combination of the third structure 180 and the third bearing component 182. However, those skilled in the art will understand that second and third bearing components 18 and 182 may also be releasably coupled to a stem structure, thereby eliminating the need for a third stem structure 180 which would otherwise be identical to second stem structure 14. Those skilled in the art will also understand that the lateral buttress may alternatively be coupled directly to the third stem structure 180, being either releasably attached thereto or integrally formed therewith.

Figure 8:
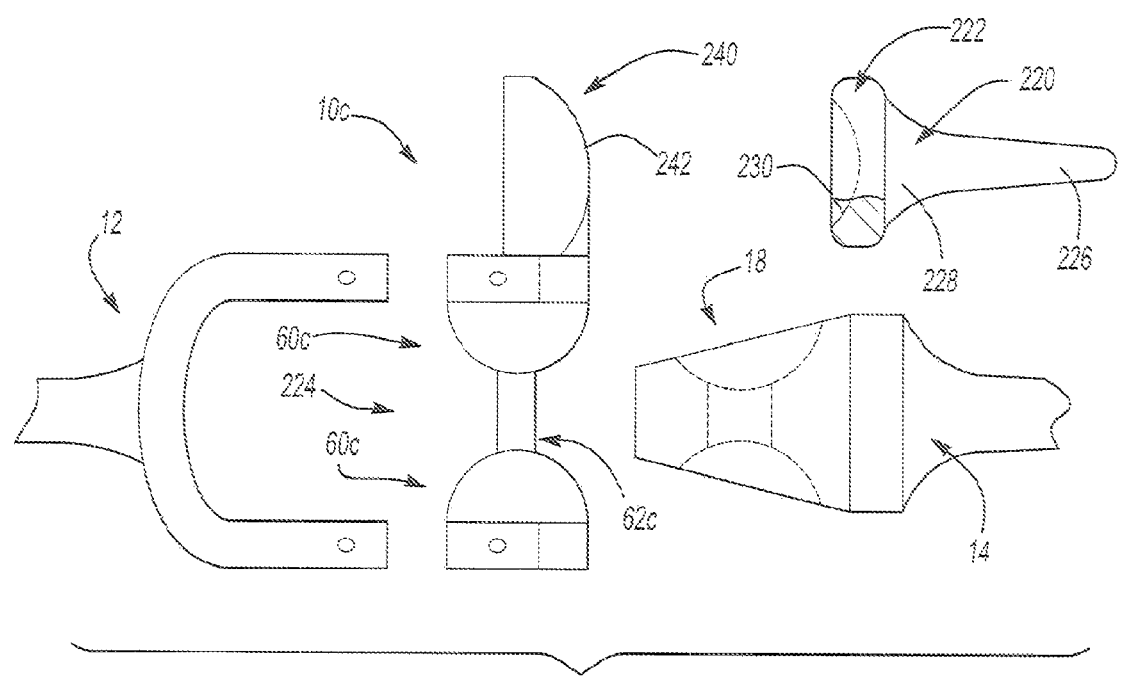
FIG. 8 is an exploded plan view of a linked prosthetic joint kit constructed in accordance with a third alternate embodiment of the first aspect of the present invention.

In FIG. 8, another linked prosthetic joint constructed in accordance with the teachings of a second aspect of the present invention is generally indicated by reference numeral 10c. Linked prosthetic joint 10c is shown to include first stem structure 12, second stem structure 14, a fourth stem structure 220, second bearing component 224. Fourth stem structure 220 includes a distal end 226 which is adapted to fit within the medullary canal of a radius and a proximal end 228 which is fixedly coupled to fourth bearing component 222. Fourth bearing component 222 includes a fourth bearing surface 230.

Fifth bearing component 224 is similar to first bearing component 16 in that it includes, for example, a pair of condyle portions 60 and a pin portion 62 which permits first and fifth bearing components 16 and 224 to be interchangeable. However, fifth bearing component 224 also includes a lateral extension 240 which is adapted to replace at least a portion of the capitellum of the humerus. Lateral extension 240 defines a fifth bearing surface 242 which is configured to mate with fourth bearing surface 230. Preferably, at least a portion of each of the fourth and fifth bearing surfaces 230 and 242 is spherically shaped to permit loads transmitted therebetween to be spread out over a relatively large area, rather than be concentrated at a single point or along a line of contact.

Figure 9:
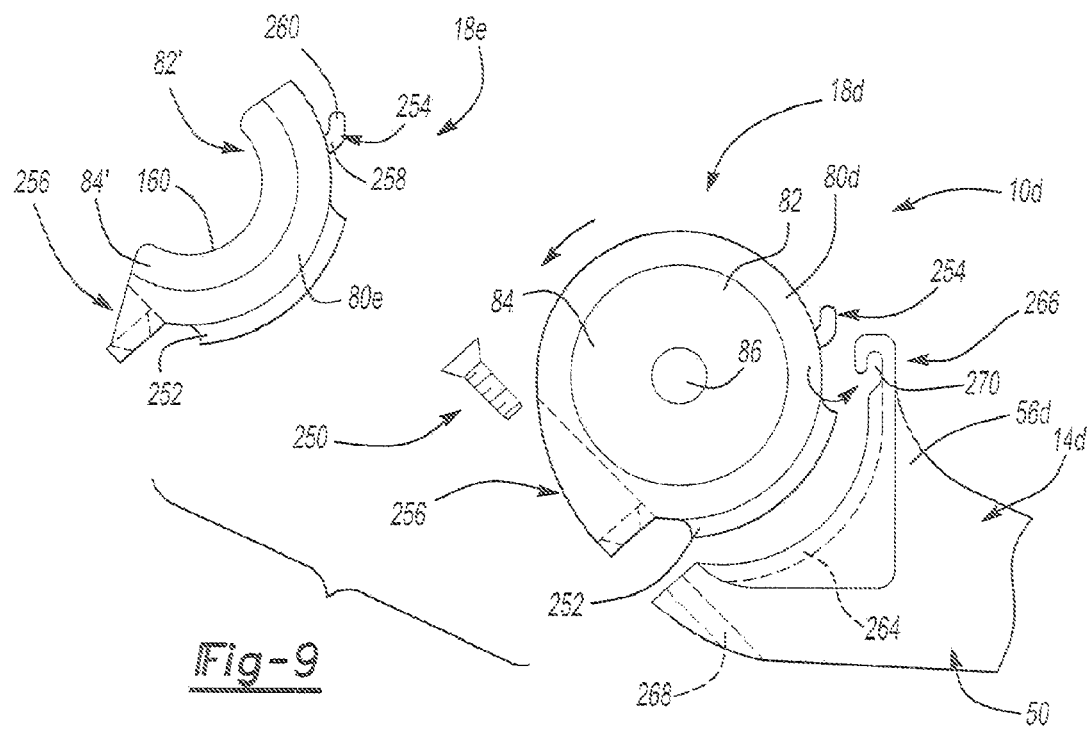
FIG. 9 is an exploded side elevation view of portion of a joint kit constructed in accordance with the teachings of a second aspect of the present invention.

In FIG. 9, a portion of a modular prosthetic joint kit constructed in accordance with the teaching of a second aspect of the present invention is generally indicated by reference numeral 10d. Modular prosthetic joint kit 10d is shown to include second stem structure 14d, second bearing component 18d, second bearing component 18e and a fastener 250.

Second bearing components 18d and 18e are similar to second bearing components 18 and 18', respectively, but are shown to be separable from second stem structure 14d. Second bearing components 18d and 18e also include a keel member 252, a clip member 254 and a fastener aperture 256 which are formed in cage portions 80d and 80e, respectively. Keel member 252 extends circumferentially around at least a portion of the perimeter of each of the cage portions 80d and 80e between clip member 254 and fastener aperture 256. Clip member 254 includes a first portion 258 which extends generally perpendicularly outward from its associated cage portion and a second portion 260 which is coupled to the distal end of first portion 258. Second portion 260 extends generally outwardly and away from first portion 258. Fastener aperture 256 is located across from clip member 254 and is sized to receive fastener 250.

Second stem structure 14d is similar to second stem structure 14 in that it includes a distal end 50 which is adapted to fit within the medullary canal of an ulna. Second stem structure 14d also includes a proximal portion 56d having a keel slot 264, a hook structure 266 and an internally threaded fastener aperture 268. Keel slot 264 is a slot that is sized to receive keel member 252 in a slip fit manner. Keel slot 264 and keel member 252 cooperate to resist relative medial-lateral motion of cage portion (e.g. 80d) relative to second stem structure 14d. Hook member 266 is generally U-shaped and defines a clip aperture 270 which is sized to receive clip member 254.

To use modular prosthetic joint kit 10d, the distal end 50 of second stem structure 14d is inserted in the medullary canal of the ulna. The modularity of the prosthetic joint kit 10d permits the surgeon to assess the patient's elbow to determine if the patient would be better served by a linked or an unlinked joint prosthesis. Once a decision has been made as to which type of joint prosthesis would better serve the patient, the surgeon selects an appropriate one of the second bearing components 18d and 18e, places its clip member 254 into the clip aperture 270, pivots the cage portion (i.e. 80d) toward the proximal end 56d of the second stem structure 14d to engage the keel member 252 into the keel slot 264, inserts the fastener 250 through the fastener aperture 256 and threadably engages the fastener 250 to the internally threaded fastener aperture 268 to fixedly but releasably couple the second stem structure 14d with the selected one of the second bearing components 18d and 18e.

Figure 10:
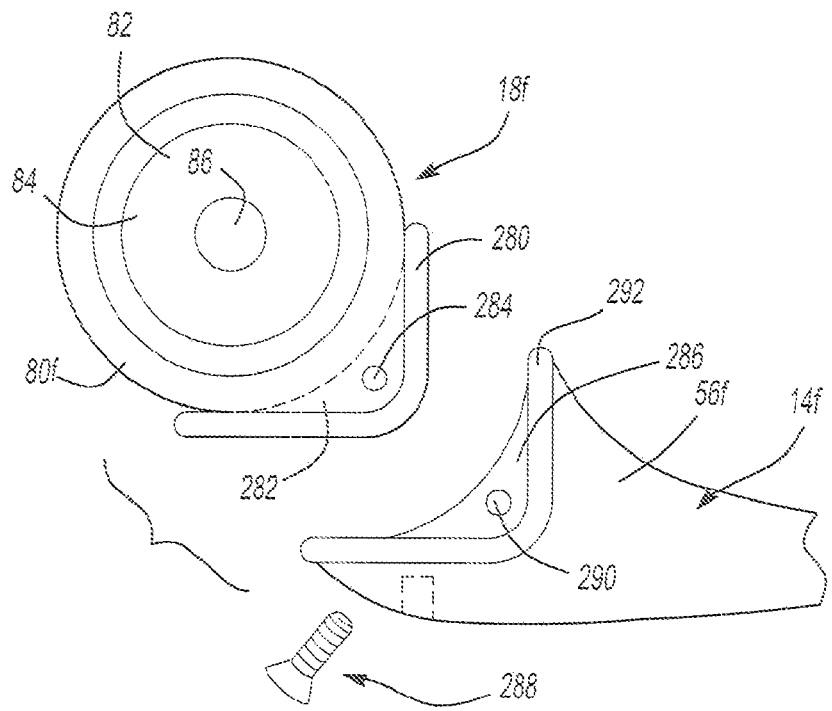
FIG. 10 is an exploded side elevation view of a portion of a joint kit constructed in accordance with a first alternate embodiment of the second aspect of the present invention.

Those skilled in the art will understand that second bearing components 18d and 18e may be coupled to second stem structure 14d in various other manners as illustrated in FIGS. 10 through 15. In FIG. 10, second bearing component 18f is shown to include a generally L-shaped tray portion 280 which is fixedly coupled to cage portion 80f. Tray portion 280 includes a keel slot 282 and a fastener aperture 284. Keel slot 282 is operable for receiving a keel member 286 formed into the proximal end 56f of second stem structure 14f. Fastener aperture 284 is operable for receiving a fastener 288 which may be threadably engaged to an internally-threaded fastener aperture 290 in the proximal end 56f of second stem structure 14f to thereby permit second bearing component 18f and second stem structure 14f to be fixedly but releasably coupled.

When coupled together, keel slot 282 and keel member 286 cooperate to resist relative medial-lateral motion of cage portion 80f relative to second stem structure 14f. Additionally, tray portion 280 cooperates with an L-shaped flange 292 to which it abuts to further resist relative rotation between second stem structure 14f and cage portion 80f.

Figure 11:
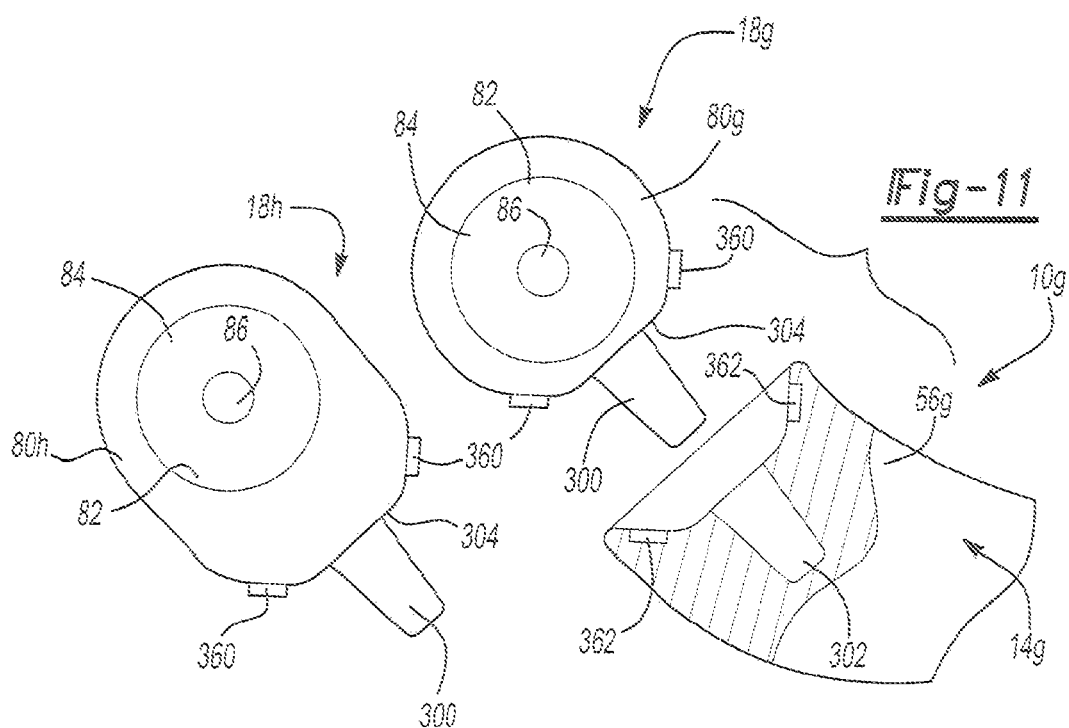
FIG. 11 is an exploded side elevation view of a portion of a joint kit constructed in accordance with a third alternate embodiment of the second aspect of the present invention.
Figure 12:
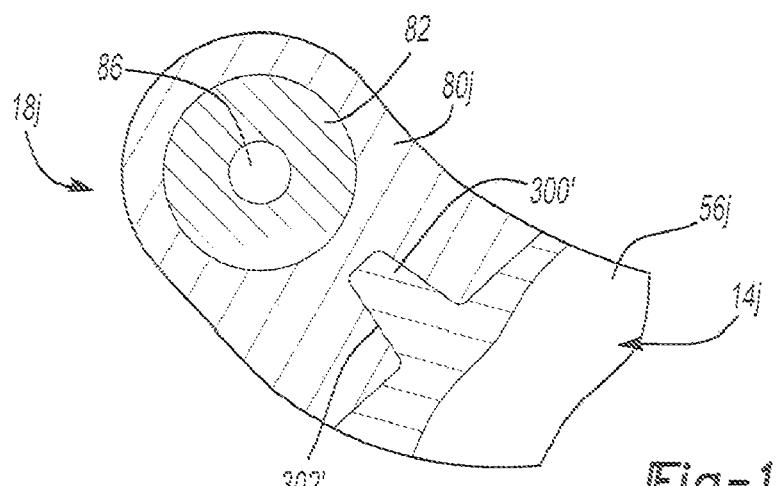
FIG. 12 is a longitudinal cross-sectional view of a portion of a joint constructed in accordance with a fourth alternate embodiment of the second aspect of the present invention.

In FIG. 11, second bearing components 18g and 18h are shown to include a stem member 300 which extends from their respective cage portions 80g and 80h. Stem member 300 is engagable with a stem aperture 302 formed into the proximal end 56g of second stem structure 14g. As shown in FIG. 12, stem member 300' may alternatively be incorporated into the proximal end 56j of second stem structure 14j and stem aperture 302' may be formed into cage portion 80j of second bearing component 18j.

To provide the surgeon with additional flexibility, second bearing component 18h is shown in FIG. 11 to be slightly longer than second bearing component 18g (i.e. the distances from the centerline of bearing member 82 to the confronting surface 304 of their respective cage portions 80g and 80h is shorter for second bearing component 18g). This variation between second bearing components 18g and 18h permits the surgeon to adjust the length of prosthesis 10g to take into account the physical characteristics of the patient's arm.

Figure 13:
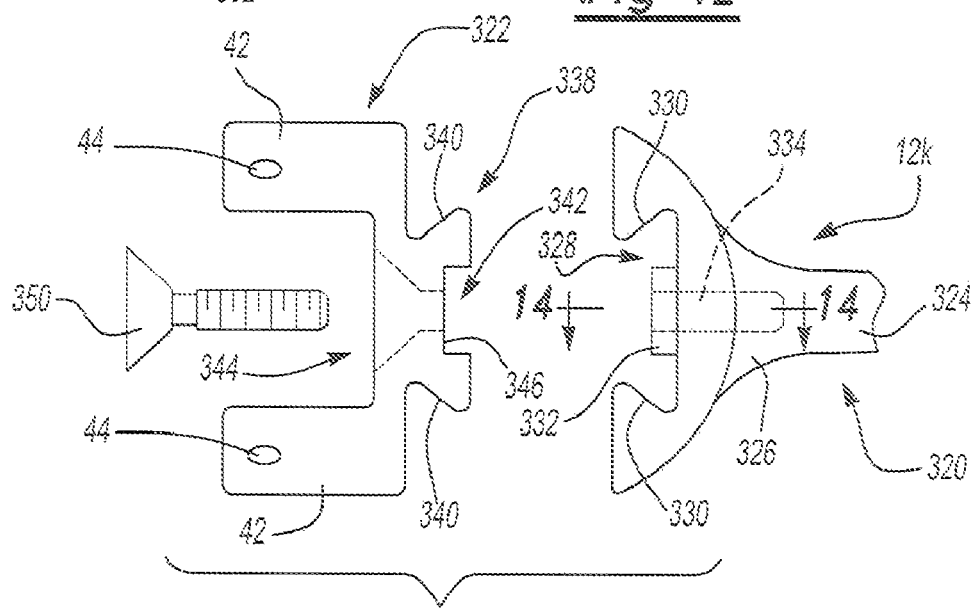
FIG. 13 is an exploded side elevation view of a portion of a joint kit constructed in accordance with a fifth alternate embodiment of the second aspect of the present invention.
Figure 14:
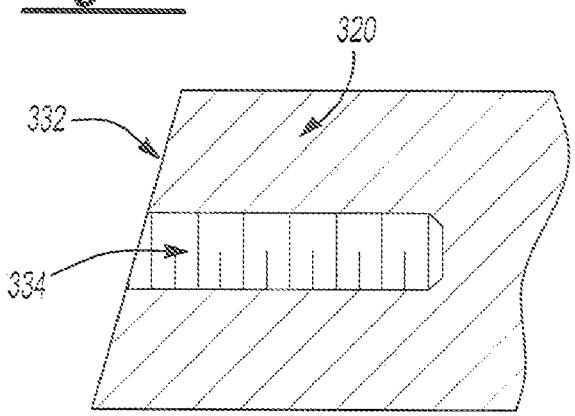
FIG. 14 is a cross-sectional view taken along the line 14-14 of FIG. 13.

Modularity may also be incorporated into first stem structure 12k as shown in FIGS. 13 and 14. First stem structure 12k is shown to include a stem member 320 and a yoke member 322. The proximal end 324 of stem member 320 is adapted to fit within the medullary canal of a humerus and the distal end 326 of stem member 320 terminates at a dovetail aperture 328 having a pair of inwardly tapering walls 330 and a tapered retaining wedge 332. An internally threaded fastener aperture 334 extends through retaining wedge 332. Yoke member 322 is shown to be similar to the distal end 32 of first stem structure 12 as it includes furcations 42 and threaded fastener apertures 44. Yoke member 322 also includes a dovetail member 338 having a pair of outwardly tapering surfaces 340, a wedge slot 342 and a through hole 344. Dovetail member 338 is configured to mate with dovetail aperture 328 such that engagement of retaining wedge 332 to the upper surface 346 of wedge slot 342 forces tapered surfaces 340 against a respective one of the inwardly tapering walls 330. A fastener 350 is inserted through hole 344 and threadably engaged to internally threaded fastener aperture 334 to fixedly but releasably couple yoke member 322 and stem member 320 together.

Referring back FIG. 11, second bearing components 18g and 18h are also shown to include a pair of tang members 360. Each of the tang members 360 extends outwardly form its respective cage portion (i.e., 80g) and in the particular embodiment illustrated, is generally rectangularly shaped. Each of the tang members 360 is sized to engage a tang recess 362 in the proximal end 56g of the second stem structure 14g. Engagement of the tang members 360 into their respective tang recess 362 inhibits relative rotation between the second stem structure 14g and the second bearing components 18g and 18h.

Figure 15:
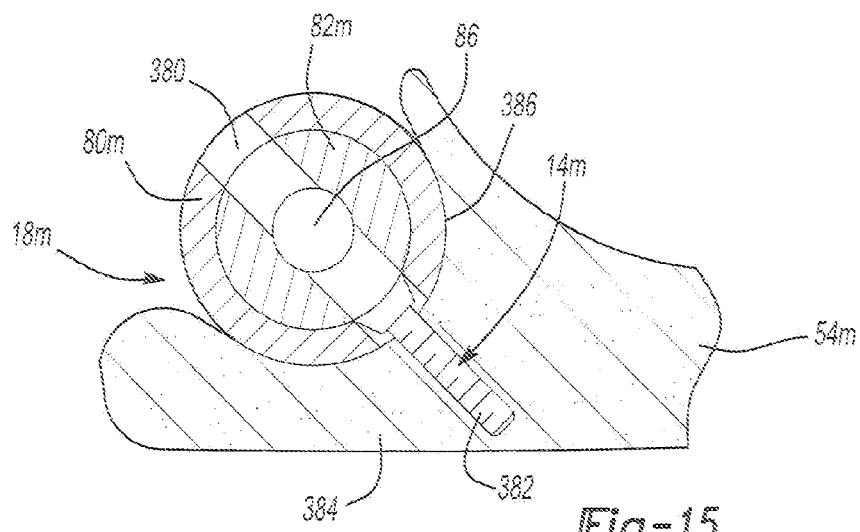
FIG. 15 is a cross-sectional view of a portion of a joint kit constructed in accordance with a sixth alternate embodiment of the second aspect of the present invention.

In FIG. 15, second bearing component 18m is shown to have a fastener aperture 380 which is formed through a bearing member 82m and cage portion 80m. Second stem structure 14m, which is a threaded fastener 382 in this embodiment, is disposed through the fastener aperture 380 in second bearing component 18m and threadably engaged to the cancellous bone 384 of the ulna 54m. Construction in this manner is advantageous in that it permits the extent of the trauma experienced by the patient to be minimized. To further this goal, the distal end 386 of cage portion 80m is shown to be generally cylindrically shaped so as to minimize the amount of bone that must be removed to prepare the ulna 54m for the second bearing component 18m.

Figure 16:
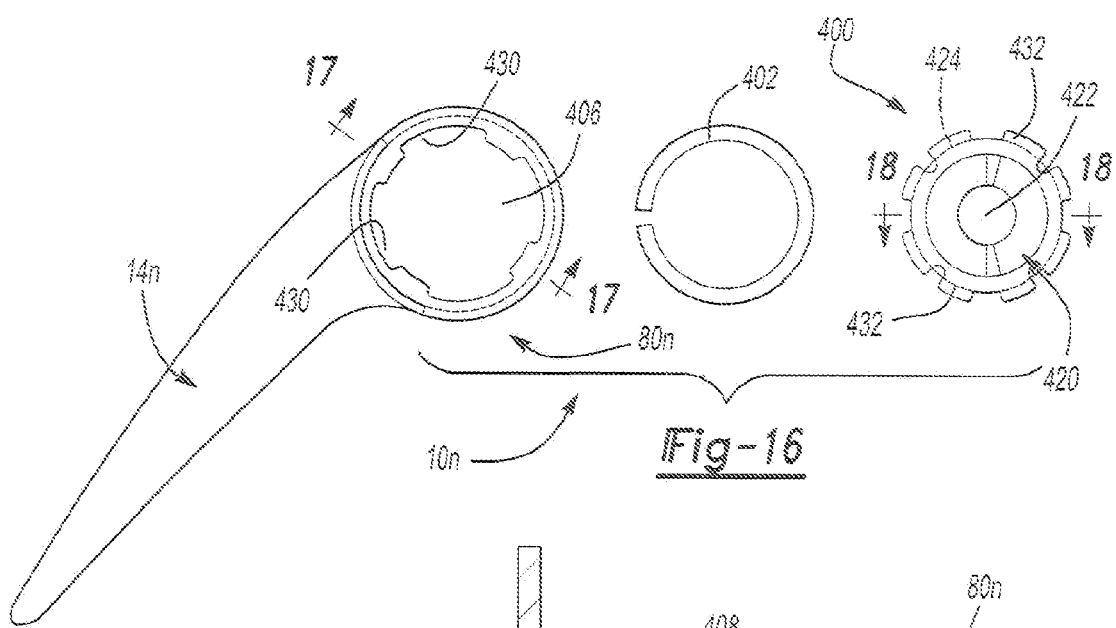
FIG. 16 is an exploded side elevation view of portion of linked prosthetic joint kit constructed in accordance with the teachings of a preferred embodiment of a third aspect of the present invention.
Figure 17:
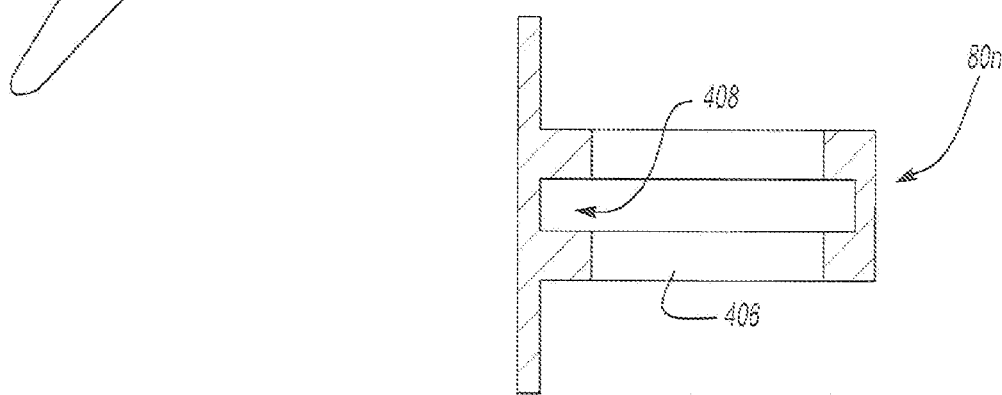
FIG. 17 is a cross-sectional view taken along the line 17-17 of FIG. 16.
Figure 18:
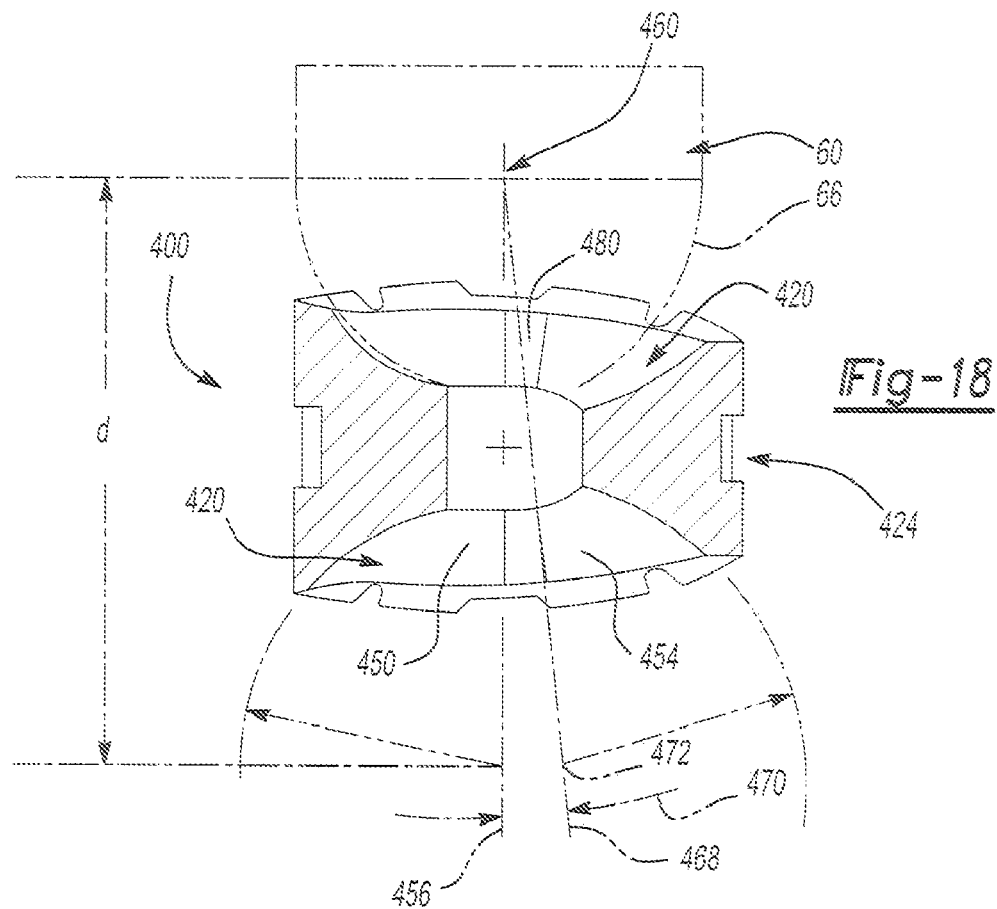
FIG. 18 is a cross-sectional view taken along the line 18-18 of FIG. 16.

In FIGS. 16 through 18, a portion of a modular prosthetic joint kit constructed in accordance with the teachings of a third aspect of the present invention is generally indicated by reference numeral 10n. Modular prosthetic joint kit 10n is shown to include a bearing insert 400, a retaining ring 402 and a second stem structure 14n having an integrally attached cage portion 80n. Cage portion 80n is shown to include a bearing aperture 406 for receiving bearing insert 400. In the particular embodiment illustrated, cage portion 80n also includes a circumferentially extending first ring groove 408 formed along the perimeter of bearing aperture 406 and operable for receiving a first portion of retaining ring 402.

Bearing insert 400 is generally cylindrically shaped, having a pair of spherical depressions 420 which collectively form a bearing surface that is configured to mate with the spherically-shaped bearing portions 66 of the first bearing component 16. Bearing insert 400 also includes a through hole 422 which is adapted to receive pin portion 62, preferably without transmitting load therebetween. A circumferentially extending second ring groove 424 is formed in the outer perimeter of bearing insert 400, the second ring groove 424 being operable for receiving a second portion of retaining ring 402. Construction in this manner is advantageous in that the surgeon may select a bearing insert 400 from a plurality of bearing inserts 400 to adapt prosthetic joint 10n to the patient.

In particular embodiment illustrated, bearing aperture 406 is shown to include a plurality of radially outwardly extending tab apertures 430 and bearing insert 400 is shown to include a plurality of radially outwardly extending tabs 432. If desired, a first one of the tab apertures 430 and a first one of the tabs 432 may be sized differently than the remaining tab apertures 430 and tabs 432, respectively, to key the bearing insert 400 to a specific orientation relative to second stem structure 14n.

With specific reference to FIG. 18, each of the pair of spherical depressions 420 includes a first spherical portion 450 and a second spherical portion 454. Each of the first spherical portions 450 are formed into bearing insert 400 along an axis 456 that is coincident with the longitudinal centerline of the bearing insert 400. Each of the first spherical portions 450 are formed by a spherical radius approximately equal in magnitude to the spherical radius which defines the spherically-shaped bearing portion 66 of each of the condyle portions 60 of first bearing component 16. The distance between the spherical radii along axis 456 is equal to a predetermined distance, d.

The centerpoint 456 of the spherical radius that defines one of the first spherical portions 450 is employed to generate the second spherical portion 454 on the opposite face of the bearing surface. A second centerline 468 is constructed from centerpoint 460 toward the opposite face at a predetermined constraint angle 470, such as 3.5 degrees. The spherical radius that defines the second spherical portion 454 on the opposite face is generated from a second centerpoint 472 which is positioned along the second centerline 468 at a distance d from centerpoint 460. Construction of bearing insert 400 in this manner permits first bearing component 16 to rotate about centerline 456, as well as to pivot relative to bearing insert 400 about the spherically-shaped bearing portion 66 of each of the condyle portions 60.

A transition zone 480 is formed between each of the first and second spherical portions 450 and 454 wherein a radius is formed at the intersection of the radii which define the first and second spherical portions 450 and 454 to "soften" the transition between the first and second spherical portions 450 and 454 to render the movement of the condyle portions 60 over the first and second spherical portions 450 and 454 more comfortable to the patient.

Those skilled in the art will understand that the degree of the constraint may be defined by the constraint angle. Accordingly, modular prosthetic joint kit 10n preferably includes a plurality of bearing inserts 400, each having a bearing surface with a second spherical portion 454 that is defined by a different constraint angle. Those skilled in the art will also understand that the degree of the constraint may be additionally or alternatively defined by a constraint characteristic, which is illustrated in FIGS. 19A and 19D.

Figure 19A:
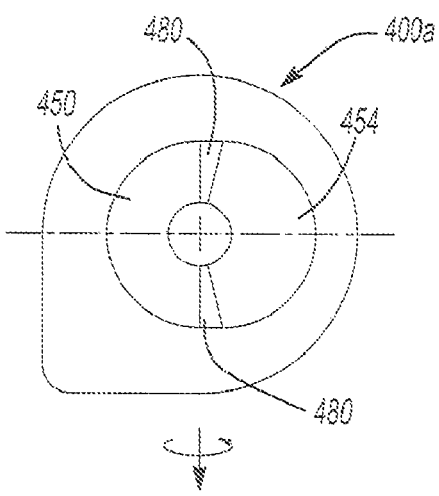
FIGS. 19A through 19D are side elevation views of bearing inserts constructed with varying degrees of varus/valgus constraint.
Figure 19B:
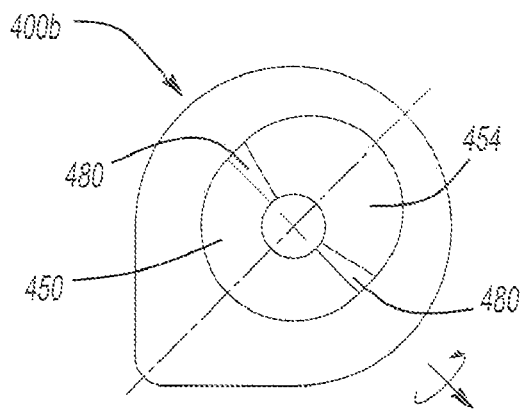
Figure 19C:
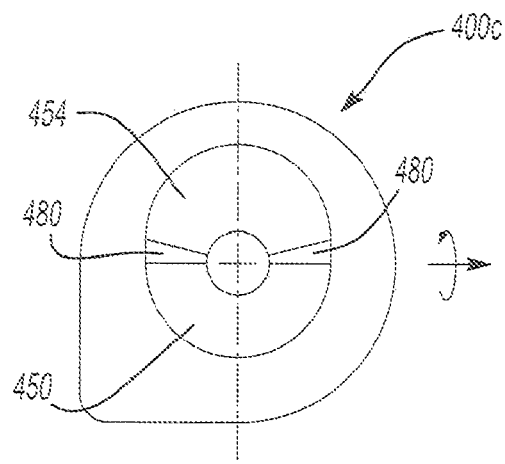
Figure 19D:
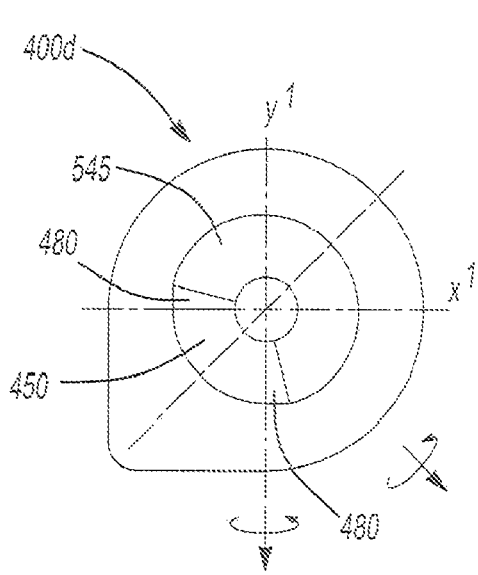

In FIG. 19A, bearing insert 400a has a first predetermined constraint characteristic orientation wherein the centerlines which define the radii which define first and second spherical portions 450 and 454 are contained in a plane which is generally perpendicular to the longitudinal axis of the ulna. Construction of bearing insert 400a in this manner provides a varying degree of axial constraint. In FIG. 19B, bearing insert 400b has a second predetermined constraint characteristic wherein the centerlines which define the radii which define first and second spherical portions 450 and 454 are contained in a plane which is at approximately 45° to the longitudinal axis of the ulna. Construction of bearing insert 400b in this manner provides a varying degree of a combination of axial and varus/valgus constraint. In FIG. 19C, bearing insert 400c has a third predetermined constraint characteristic wherein the centerlines which define the radii which define first and second spherical portions 450 and 454 are contained in a plane which is generally parallel the longitudinal axis of the ulna. Construction of bearing insert 400c in this manner provides a varying degree of varus/valgus constraint. In FIG. 19D, bearing insert 400d is constructed in a manner that is generally similar to that of bearing inserts 400a, 400b and 400c except that the constraint angle employed to construct bearing insert 400d is rotated from point x1 to y1 as indicated in FIG. 19d. As a result, there is no single line of orientation in which the constraint is limited. Construction of bearing insert 400d in this manner provides a varying degree of constraint in both an axial direction and a varus/valgus direction.

Figure 20A:
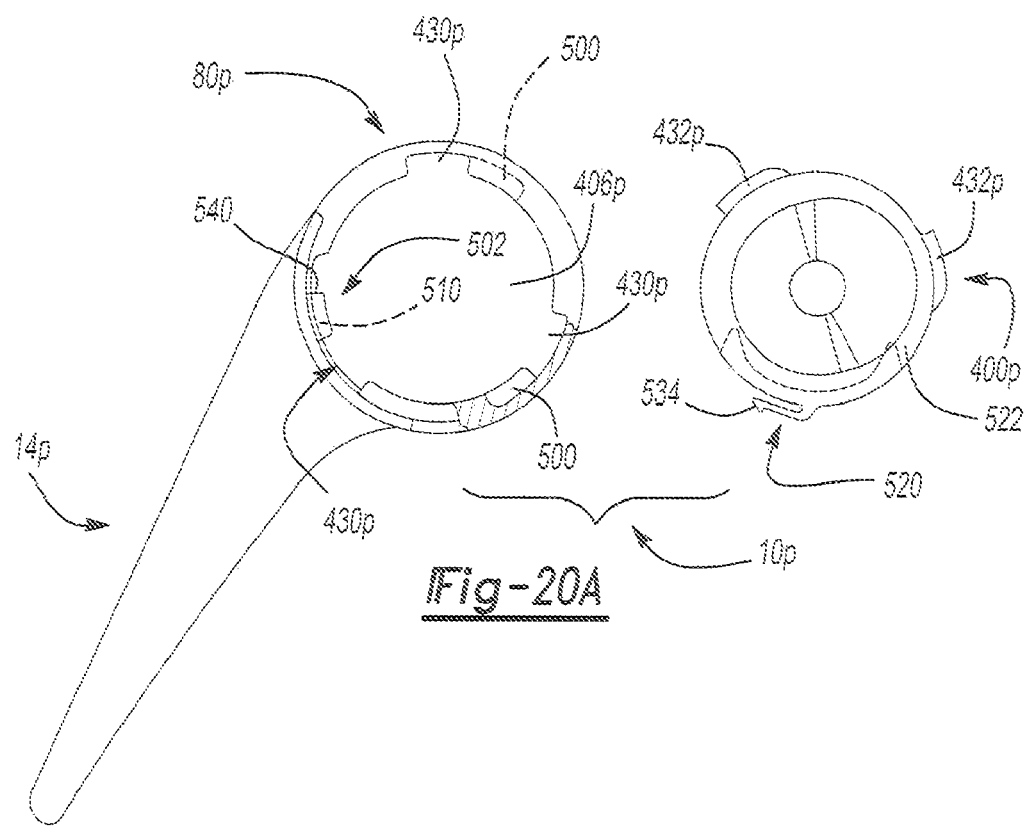
FIG. 20A is an exploded side elevation view portion of a linked prosthetic joint kit constructed in accordance with the teachings of a first alternate embodiment of the third aspect of the present invention.
Figure 20B:
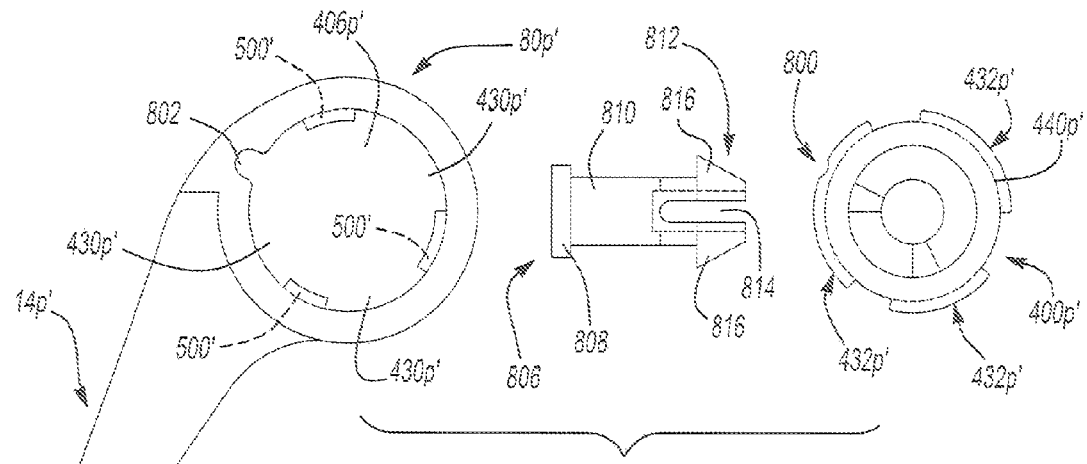
FIG. 20B is an exploded side elevation view of a portion of a linked prosthetic joint constructed in accordance with the teachings of second alternate embodiment of the third aspect of the present invention.
Figure 20C:
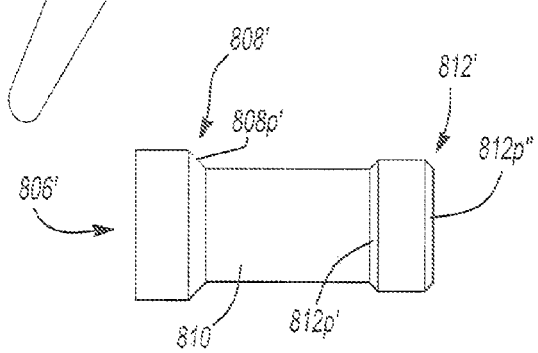
FIG. 20C is a side view of an alternately constructed pin for linking the bearing structures of the second alternate embodiment of the third aspect of the present invention.
Figure 21:
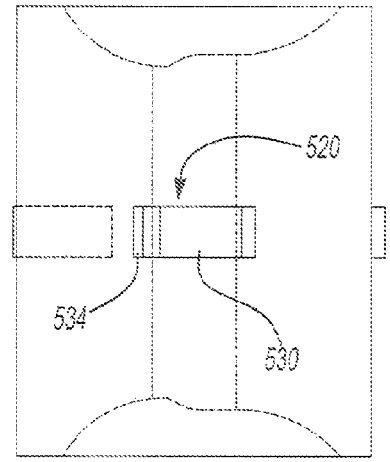
FIG. 21 is a bottom plan view of a portion of the linked prosthetic joint kit of FIG. 20 illustrating the bearing insert in greater detail.
Figure 22:
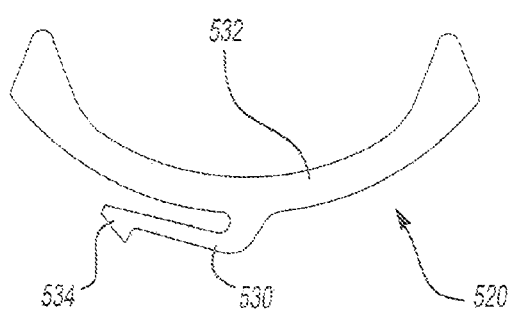
FIG. 22 is a side elevation view of a portion of the linked prosthetic joint kit of FIG. 20 illustrating the clip in greater detail.

In FIGS. 20 through 22, a portion of a modular prosthetic joint kit constructed in accordance with the teachings of an alternate embodiment of the third aspect of the present invention is generally indicated by reference numeral 10p. Modular prosthetic joint kit 10p is similar to modular prosthetic joint kit 10n in that it includes a bearing insert 400p and a second stem structure 14p having a integrally attached cage portion 80p.

Cage portion 80p is shown to include a bearing aperture 406p for receiving bearing insert 400p. In the particular embodiment illustrated, cage portion 80p includes a plurality of tab apertures 430p, a plurality of tab slots 500 and a hook structure 502. Each of the tab apertures 430p extends axially through cage portion 80p and circumferentially around a portion of bearing aperture 406p. Each of the tab slots 500 intersects one of the tab apertures 430p and extends circumferentially around a portion of bearing aperture 406p away from its associated tab aperture 430p. Hook structure 502 is adjacent one of the tab apertures 430p and extends radially inwardly and circumferentially around a portion of bearing aperture 406p. A clip slot 510 is formed circumferentially through hook structure 502.

Bearing insert 400p is generally similar to bearing insert 400 except for the configuration of the plurality of tabs 432p and the incorporation of a clip structure 520 into a bearing body 522. Each of the plurality of tabs 432p is relatively thin and do not extend axially across bearing insert 400p. This permits the tabs 432p of bearing insert 400p to be aligned to a tab aperture 430p and bearing insert 400p to be rotated so that each of the tabs 432p is disposed within one of the tab slots 500 to thereby prevent bearing insert 400p from moving in an axial direction.

Clip structure 520 is preferably a metal or plastic fabrication which is suitable for molding into bearing body 522. Clip structure 520 includes an arm structure 530 which extends from a clip body 532 and terminates at its distal end at a hook member 534. Clip structure 520 is configured and incorporated into bearing body 522 such when bearing insert 400p is rotated to engage tabs 432p into tab slots 500, arm structure 530 simultaneously engages clip slot 510 in hook structure 502. Rotation of bearing insert 400p to a predetermined rotational position relative to hook structure 502 permits hook member 534 to engage an edge 540 of hook structure 502. Arm structure 530 resiliently biases hook member 534 against edge 540, thereby inhibiting rotation of bearing insert 400p which would cause tabs 432p to disengage tab slots 500.

In FIG. 20B, bearing insert 400p' is illustrated to be configured similarly to bearing insert 400p except that a locking aperture 800 is formed into one of the tabs 432p'. Bearing insert 400p' is inserted into bearing aperture 406p' aligned such that each of the tabs 432p' is aligned to an associated one of the tab apertures 430p'. Bearing insert 400p' is then rotated so that each of the tabs 500p' is disposed within one of the tab slots 440p' and locking aperture 800 is aligned to a corresponding locking aperture 802 formed in the integrally attached cage portion 80p' of second stem structure 14p'. Engagement of tabs 500' into their respective tab slots 440p' prevents bearing insert 400p' from moving in an axial direction. Alignment of locking apertures 800 and 802 to one another permits a pin 806 to be inserted therethrough to prevent bearing insert 400p' from rotating relative to integrally attached cage portion 80p'. In the particular embodiment illustrated, pin 806 includes a head portion 808, a body portion 810 and an end portion 812. Head portion 808 has a diameter which is larger than the diameter of the hole formed by locking apertures 800 and 802. Body portion 810 is preferably smaller in diameter than the diameter of the hole formed by locking apertures 800 and 802.

A plurality of slots 814 are formed in end portion 812 which creates a plurality of fingers 816 which are flexible relative to the longitudinal axis of pin 806. Fingers 816 flex inwardly toward the longitudinal axis of pin 806 when pin 806 is inserted to locking apertures 800 and 802, eliminating the interference therebetween to permit the fingers 816 of end portion 812 to pass through integrally attached cage portion 80p' and bearing insert 400p'. Once the fingers 816 have passed through integrally attached cage portion 80p' and bearing insert 400p', they flex outwardly away from the longitudinal axis of pin 806 to inhibit the unintended withdrawal of pin 806 form locking apertures 800 and 802. Intended withdrawal of pin 806 from locking apertures 800 and 802 may be effected through the flexing of fingers 816 inwardly toward the longitudinal axis of pin 806.

Those skilled in the art will understand, however, that the pin 806 for linking first and second stem structures 12 and 14p' may be constructed differently. As shown in FIG. 20C, for example, the pin 806' includes head and end portions 808' and 812' having chamfered abutting surfaces 808p' and 812p', respectively. Additionally, the end portion 812' includes a chamfered lead portion 812p''. Pin 806' is installed by simply pressing it through the bearing insert 400p'.

Figure 23:
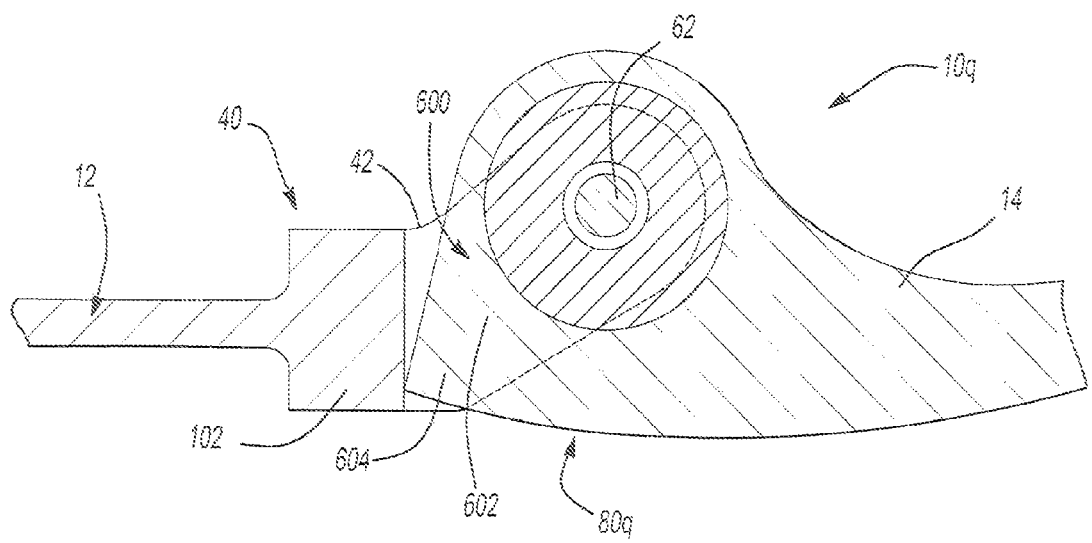
FIG. 23 is a longitudinal cross-sectional view of a linked prosthetic joint kit constructed in accordance with the teachings of a preferred embodiment of a fourth aspect of the present invention.
Figure 24:
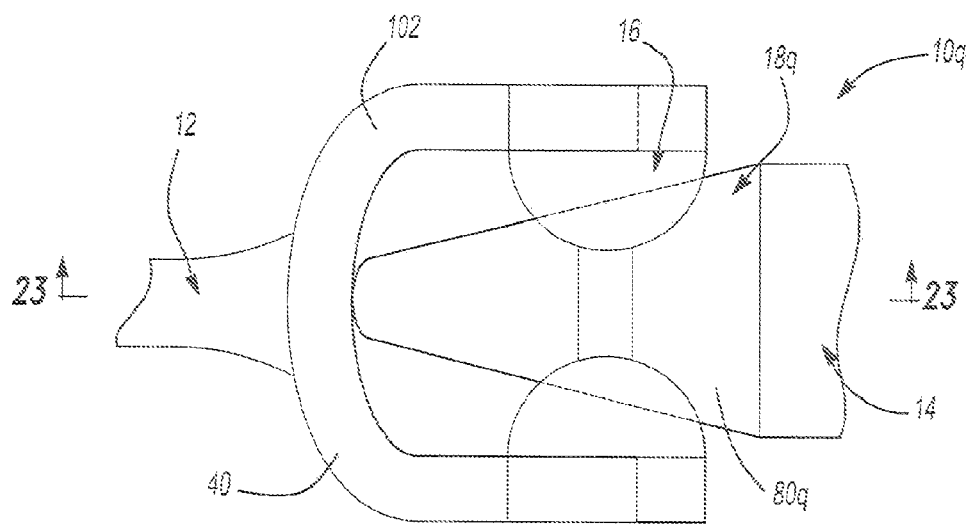
FIG. 24 is a top plan view of the linked prosthetic joint kit of FIG. 23.

In FIGS. 23 and 24, a portion of a modular prosthetic joint kit constructed in accordance with the teachings of a fourth aspect of the present invention is generally indicated by reference numeral 10q. Prosthetic joint kit 10q is shown to include first stem structure 12, second stem structure 14, first bearing component 16 and second bearing component 18q. Second bearing component 18q is substantially similar to second bearing component 18 except that cage portion 80q is shown to include an cam structure 600. Cam structure 600 includes a lobe member 602 that extends radially outwardly and terminates at a tip 604. Lobe member 602 is configured such that tip 604 contacts the base 102 of U-shaped member 40 to inhibit further relative rotation between first and second stem structure 12 and 14 when the first and second stem structures 12 and 14 are placed in a position corresponding to the maximum extension of a patient's arm. Configuration of second bearing component 18q in this manner is advantageous in that it limits the amount by which a patient may rotate their ulna relative to their humerus to prevent hyperextension of the joint.

Figure 25:
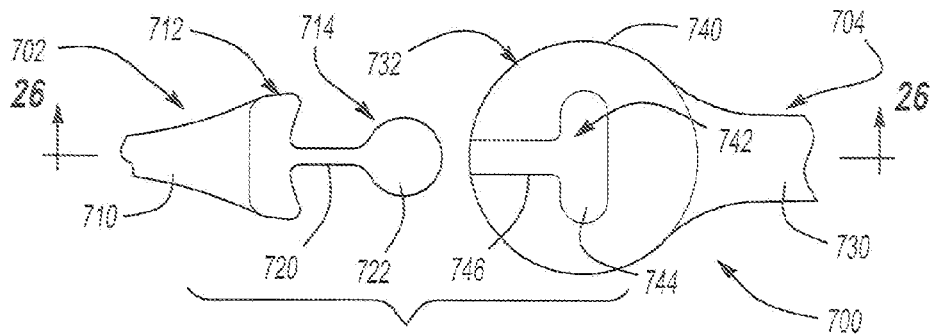
FIG. 25 is an exploded top plan view of a linked prosthetic joint kit constructed in accordance with the teachings of a preferred embodiment of a fifth aspect of the present invention.
Figure 26:
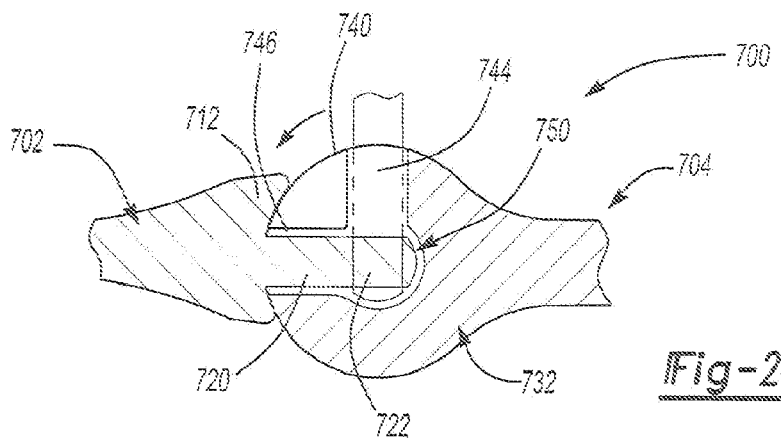
FIG. 26 is a longitudinal cross-sectional view of the linked prosthetic joint kit of FIG. 25.

In FIGS. 25 and 26, a portion a modular prosthetic joint kit constructed in accordance with the teaching of a fifth aspect of the present invention is generally indicated by reference numeral 700. Prosthetic joint kit 700 is shown to include a first stem structure 702 and a second stem structure 704. First stem structure 702 includes a stem member 710, the distal end of which is configured to fit within the medullary canal of an ulna. A first bearing 712 and a coupling structure 714 are incorporated into the proximal end of first stem structure 702. First bearing structure 712 is generally spherically shaped. Coupling structure 714 includes a link member 720 and a retainer member 722. Link member 720 is fixedly coupled to first bearing 712 at a first end and to retaining structure 722 at a second end with link member 720 extending therebetween along an axis generally coincident the longitudinal axis of first stem structure 702. Retaining structure 722 is illustrated to be spherically shaped with flattened ends. According to various embodiments a stop member 722' is generally cylindrically shaped and the coupling member 714 is coupled to the stop member 722' along an axis that is generally perpendicular to a longitudinal axis of the stop member.

Second stem structure 704 is shown to include a stem member 730 with a proximal end that is configured to fit within the medullary canal of a humerus. A second bearing structure 732 is incorporated into the distal end of second stem structure 704. Second bearing structure 732 includes a generally spherical second bearing surface 740 and a T-shaped coupling aperture 742. A first portion 744 of coupling aperture 742 has a width which is larger than the width of retaining structure 722. First portion 744 is oriented at a position of maximum flexion. In the particular embodiment illustrated, the position of maximum flexion is illustrated to be about 90° to the longitudinal axis of second stem structure 704. However, those skilled in the art will understand that the position of maximum flexion may be tailored in a desired manner and many range as high to an angle of approximately 135° to 150° to the longitudinal axis of second stem structure 704, depending on the particular application. A second portion 746 of coupling aperture 742 has a width which is slightly larger than that of link member 720. Second portion 746 extends circumferentially around a portion of second bearing surface 740 in a plane that coincides with the longitudinal axis of second stem structure 704. The first and second portions 744 and 746 of coupling aperture 742 intersect and terminate at spherically shaped cavity 750.

To use prosthetic joint kit 700, first and second stem structures 702 and 704 are inserted into the medullary canals of the ulna and humerus, respectively. First stem structure 702 is then positioned proximate the first portion 744 of coupling aperture 742 and retaining structure 722 is inserted through first portion 744 and into spherically shaped cavity 750. At this point, first and second bearing surfaces 712 and 740 are in contact with one another and transmit load therebetween rather than through coupling structure 714. Coupling of first and second stem structures 702 and 704 is complete when first stem structure 720 is rotated into second portion 746. In this position, first and second stem structures 702 and 704 are linked or constrained since the width of retaining portion 722 is larger than the width of second portion 746 and thereby prevents the withdrawal of first stem structure 702 from coupling aperture 742.

Figure 27:
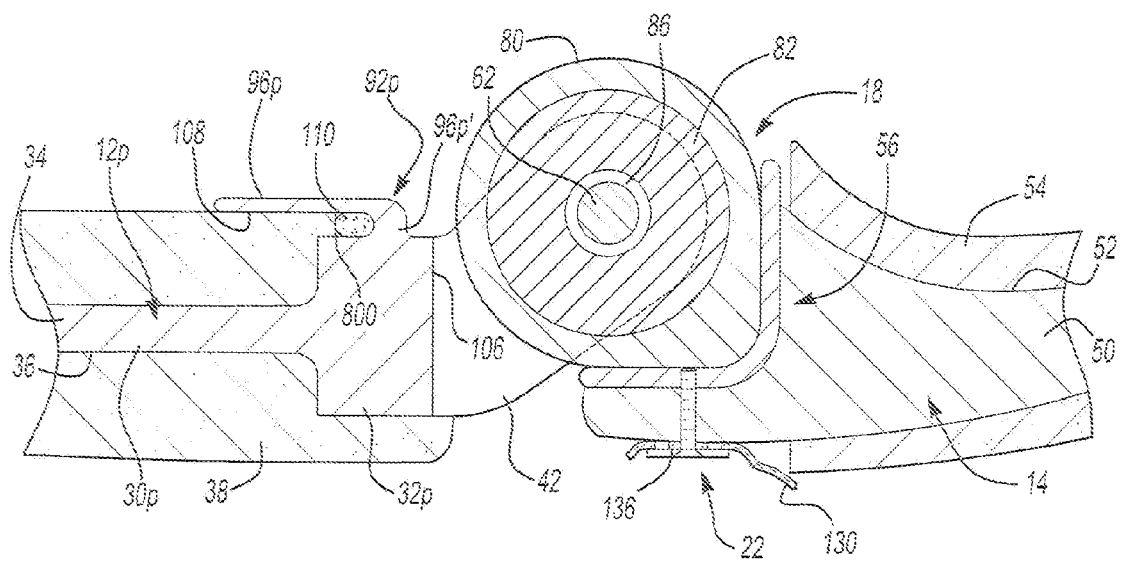
FIG. 27 is a longitudinal cross-sectional view similar to that of FIG. 2, but illustrating the stem with an integrally-formed flange for compressing a bone graft.
Figure 26A:
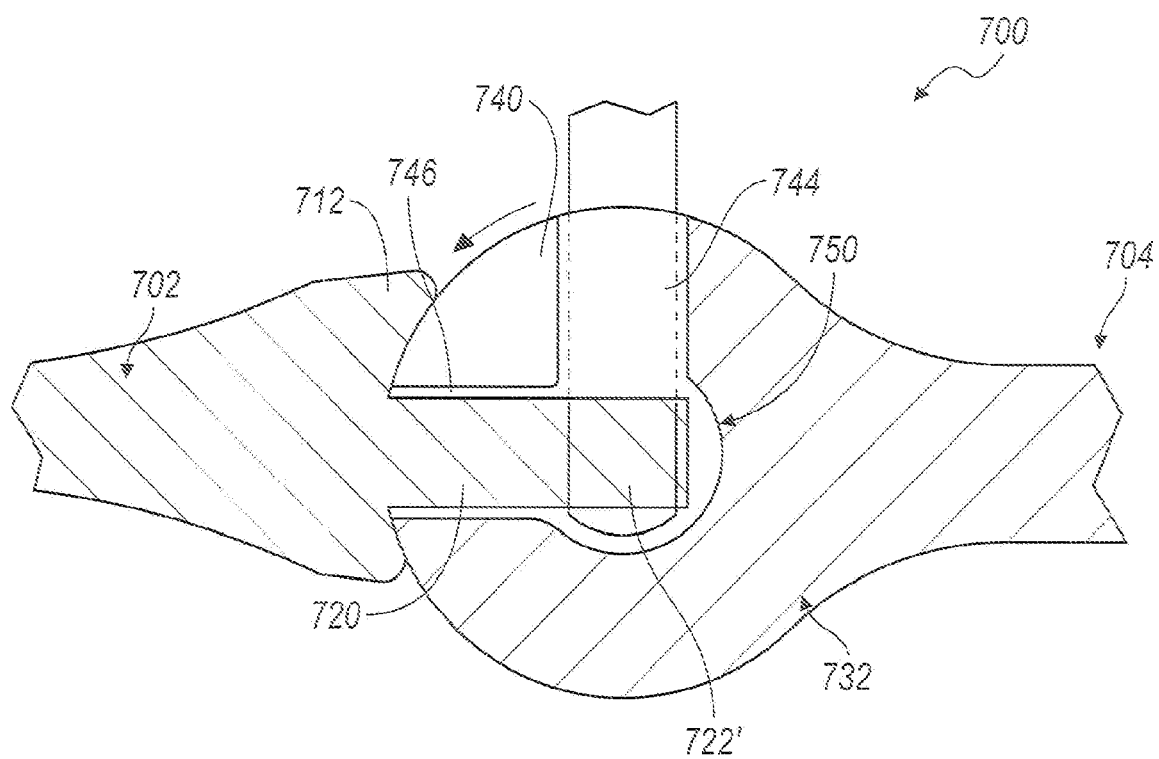
FIG. 26a is a longitudinal cross-sectional view of the linked prosthetic joint kit according to various embodiments.

While the prosthetic joint devices 10 and 10a have been illustrated as having modular flanges 20 that are fixedly but removably coupled to the first stem structure 12, those skilled in the art will understand that the invention, in its broader aspects, may be constructed somewhat differently. For example, the stem structure and modular flange may be unitarily formed as shown in FIG. 27. In this embodiment, the stem 12p is illustrated to be similar to the stem 12, but includes a flange structure 92p having a flange member 96p and a coupling portion 96p' that couples the flange member 96p to the distal portion 32p of the stem 12p. The flange member 96p is generally parallel the stem member 30p and is employed to compress a bone graft against the stem member 30p. Unlike the modular flange 20 that was described in detail, above, the flange structure 92p must be fitted over a bone graft 110 or the bone graft must be placed into the aperture 800 between the stem member 30p.

Figure 28:
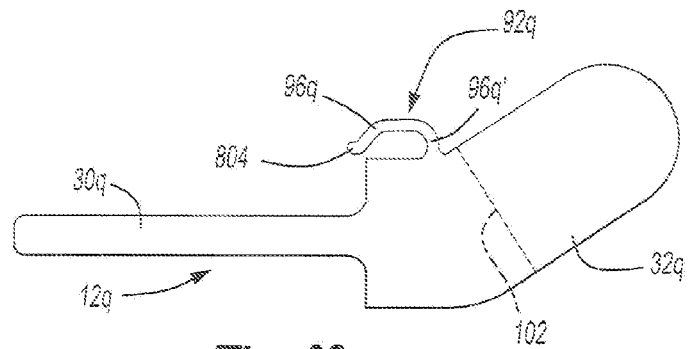
FIG. 28 is a side view illustrating a stem with an integrally-formed, resilient flange for compressing a bone graft.
Figure 29:
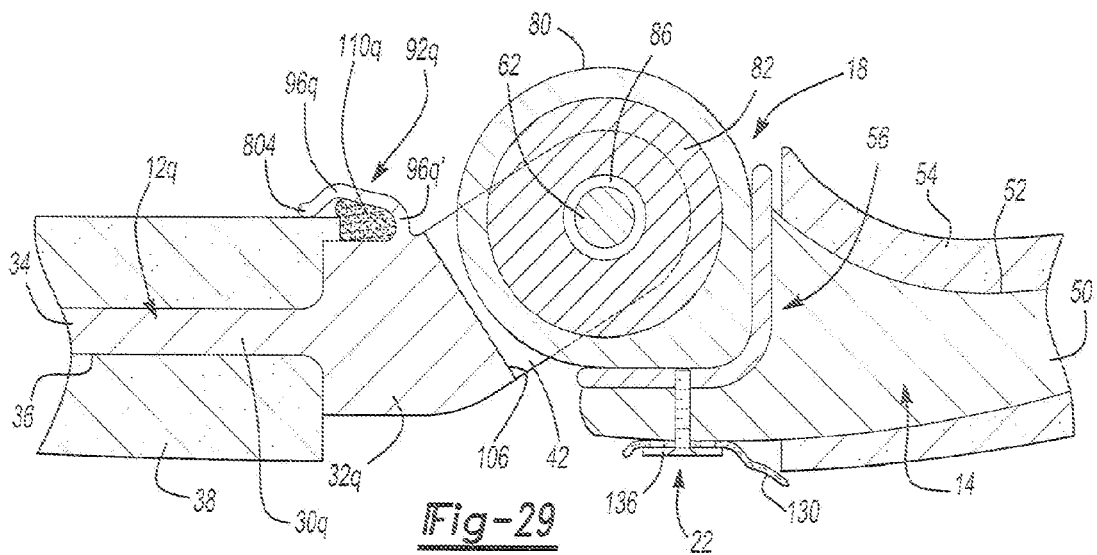
FIG. 29 is a longitudinal cross-sectional view similar to that of FIG. 2, but illustrating the stem of FIG. 28.
Figure 30:
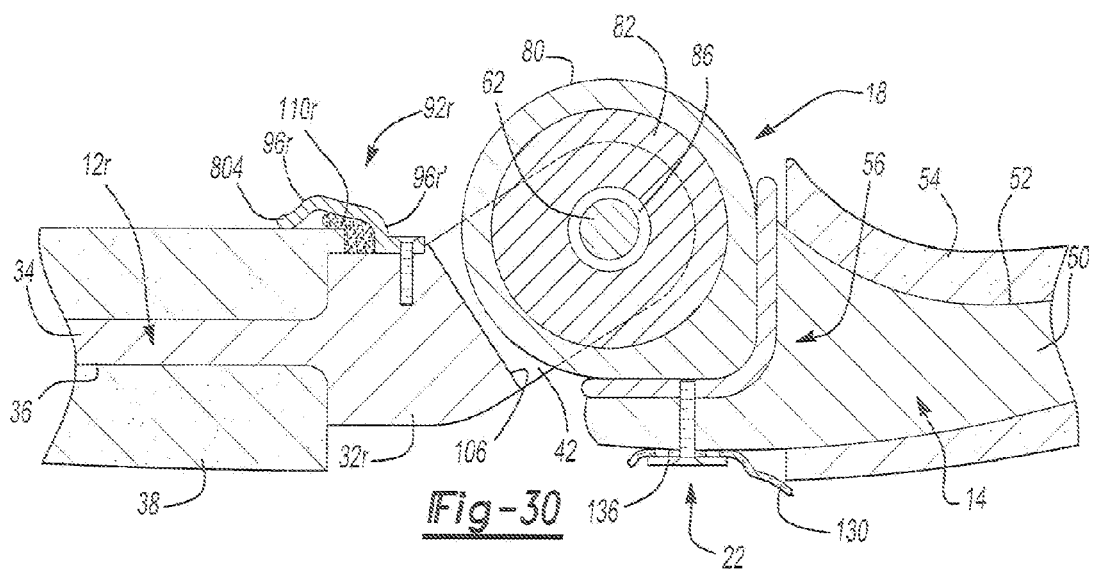
FIG. 30 is a longitudinal cross-sectional view similar to that of FIG. 29, but illustrating the resilient flange as being fixedly but removably coupled to the stem.

Another example of an integrally formed (i.e., non-removable) flange structure is illustrated in FIGS. 28 and 29. In this example, the stem 12q is illustrated to be similar to the stem 12p in that it includes a flange structure 92q having a flange member 96q and a coupling portion 96q' that couples the flange member 96q to the distal portion 32q of the stem 12q. The flange member 96q, however, is arcuately shaped and includes a contact tab 804. The flange structure 92q is formed with a predetermined degree of resiliency, which may result from the characteristics of the material from which the flange structure 92q is formed or by controlling the geometry (i.e., cross-sectional shape and area) of the flange structure 92q. The resiliency of the flange structure 92q permits the flange member 96q to act as a leaf spring that biases the contact tab 804 toward the stem member 30q. Accordingly, the flange may be employed to apply compression to the bone graft 110q without fasteners or other securing means. As illustrated in FIG. 30, those skilled in the art will readily understand, however, that a predetermined amount of resiliency may also be incorporated into a flange structure 92r that is fixedly but removably coupled to the stem 12r.

Figure 31:
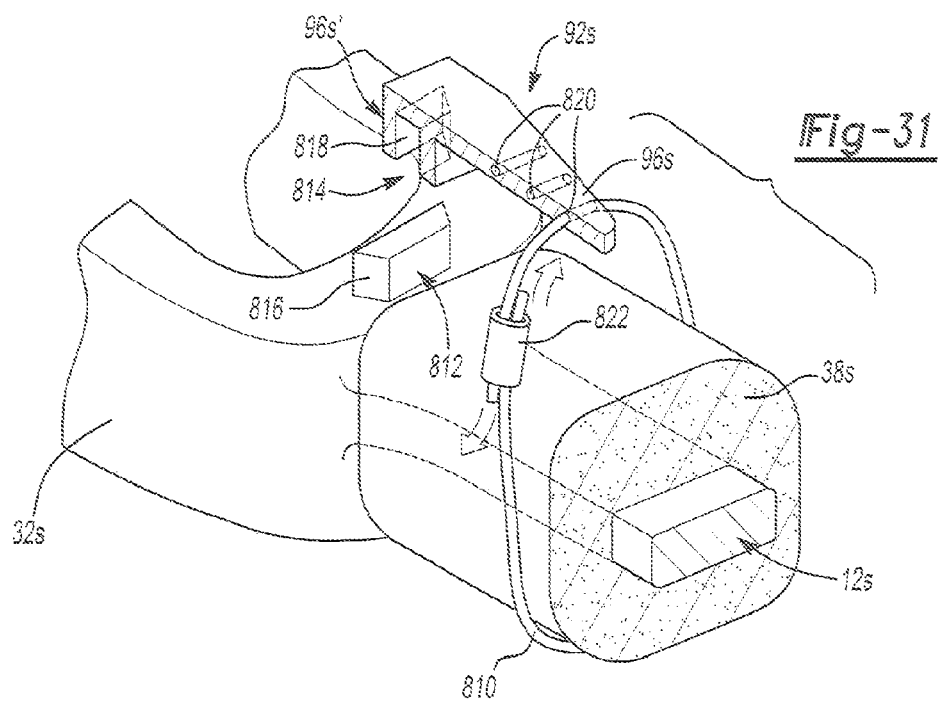
FIG. 31 is a partially broken-away exploded perspective view illustrating an alternative coupling the modular flange to the stem.
Figure 32:
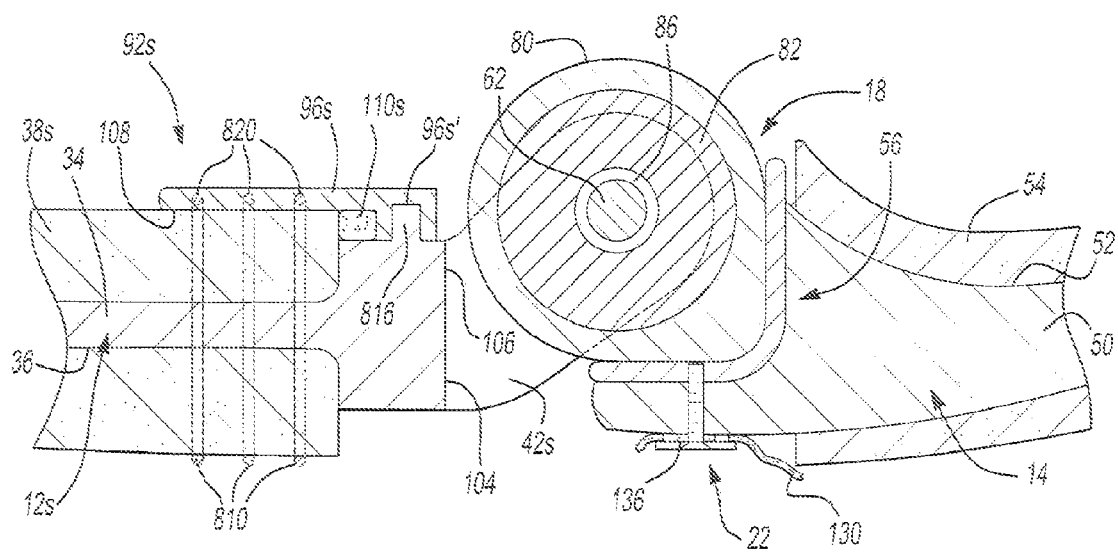
FIG. 32 is a longitudinal cross-sectional view similar to that of FIG. 2, but illustrating the alternative coupling means of FIG. 31.

Those skilled in the art will also understand that although the modular flange 20 has been illustrated as being coupled to the stem 12r via a threaded fastener 94b, the invention, in its broader aspects, may be constructed somewhat differently. For example, cable 810 are employed to fixedly but removably retain the flange structure 92s to the stem 12s as illustrated in FIGS. 31 and 32. The stem 12s is generally similar to the stem 12, but includes a first coupling feature 812 instead of the bore 100. The flange structure 92s includes a flange member 96s and a coupling portion 96s'. The coupling portion 96s' includes a second coupling feature 814 that is configured to cooperate with the first coupling feature 812 to locate the flange member 96s relative to the distal portion 32s of the stem 12s. In the example illustrated, the first coupling feature 812 is a generally trapezoidal dovetail member 816 that extends outwardly from the distal portion 32s of the stem 12s and the second coupling feature 814 is a dovetail aperture 818 that is formed into the coupling portion 96s' and sized to engage the dovetail member 816 in with a line-to-line fit (i.e., with very little or no clearance). The dovetail member 816 is preferably integrally formed onto the stem 12s but may alternatively be an independently formed component that is fixedly coupled to the distal portion 32s via an appropriate coupling means, such as threaded fasteners, press-fitting or shrink fitting.

The flange member 96s is shown to include a plurality of cross-holes 820 that extend completely through the flange member 96s in a direction that is generally perpendicular the longitudinal axis of the flange member 96s. The cross-holes 820 are sized to receive the cable 810. As those skilled in the art will understand, the cable 810 are first secured around the humerus 38s and the ends of the cable 810 are loosely secured via an appropriate coupling device, such as a cable sleeve 822. The cables 810 are then tensioned to urge the flange member 96s against the humerus 38s and compress the bone graft 110s by a predetermined amount. Thereafter, the coupling device is employed to fix the ends of the cables relative to one another so as to maintain tension in the cables 810.

While the first and second coupling features 812 and 814 have been illustrated as being a dovetail member 816 and a dovetail aperture 818, respectively, those skilled in the art will appreciate that the first and second coupling features 812 and 814 can be constructed somewhat differently. As illustrated in FIG. 33, for example, the first coupling feature 812t is illustrated as being a pair of pins 830 that are fixedly coupled to the distal portion 32t of the stem 12t and the second coupling feature 814t is illustrated to be a corresponding pair of holes 832 that are formed into the coupling portion 96t. The pins 830 are preferably press-fit or shrunk fit into corresponding holes (not specifically shown) that are formed into the distal portion 32t of the stem 12t but may be secured via other fastening means, such as welding, bonding, or threaded engagement where the pins 830 have a threaded portion that is threadably engaged to the holes in the distal portion 32t. Alternatively, the pins 830 may also be integrally formed as a part of the stem 12t.

Figure 35:
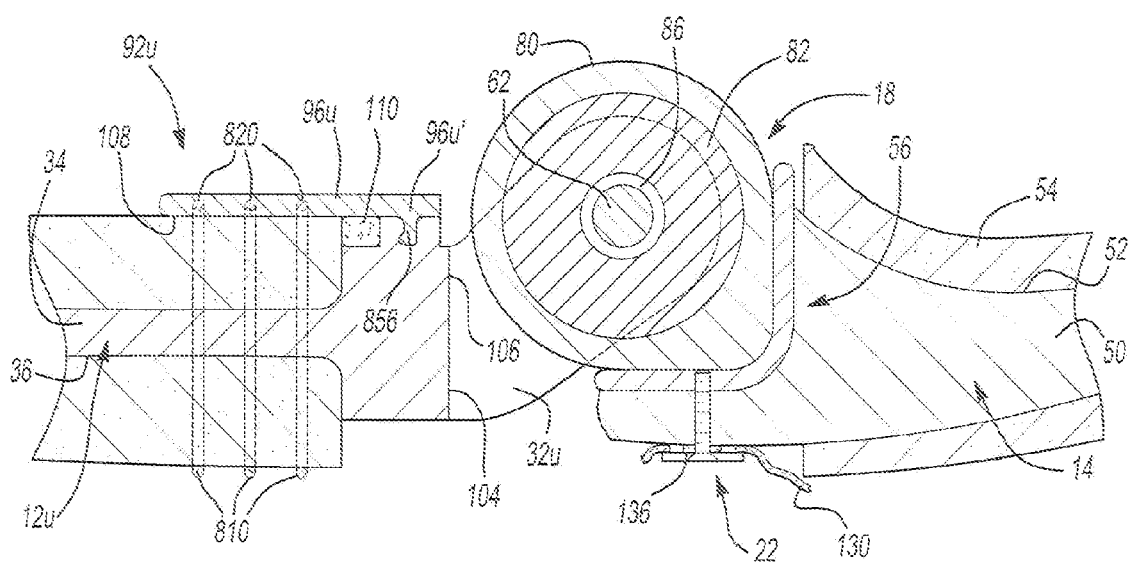
FIG. 35 is a longitudinal cross-sectional view similar to that of FIG. 2, but illustrating the alternative coupling means of FIG. 34.

Another example is illustrated in FIGS. 34 and 35, where the first coupling feature 812u is shown to include a mounting structure 840 with an arcuate mounting aperture 842 and the second coupling feature 814u is shown to include an attachment hook 846. The mounting structure 840 is coupled to the distal portion 32u of the stem 12u and extends generally perpendicularly outwardly from the base 102u of the U-shaped portion 40u. The mounting aperture 842 is generally J-shaped and includes a first portion 850, which is aligned generally perpendicular to the base 102u, and an arcuate second portion 852, which extends away from the stem member 34u and the base 102u. The attachment hook 846 is also generally J-shaped, being configured to matingly engage the mounting aperture 842. In this regard, the attachment hook 846 includes a leg portion 856 that extends downwardly from the flange member 96u and an arcuate base member 858.

In coupling the first and second coupling features 812u and 814u, flange structure 92u is initially positioned relative to the stem 12u such that the base member 858 is disposed within the first portion 850 of the mounting aperture 842. The flange structure 92u is then rotated downwardly toward the stem member 34u to permit the base member 858 to engage the second portion 852 of the mounting aperture 842. The cables 810 are thereafter employed to fix the flange structure 92u relative to the stem 12u.

While the invention has been described in the specification and illustrated in the drawings with reference to a preferred embodiment, it will be understood by those skilled in the are that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the foregoing description and the appended claims.

What is claimed is:

1. A prosthetic joint kit comprising:
   a first stem structure having a first end adapted to fit within a medullary canal of a first bone;
   a first bearing component coupled to the first stem structure, the first bearing component having first and second condyle portions, each of the first and second condyle portions being at least partially spherically shaped;
   a second stem structure having a second end that is adapted to fit within a medullary canal of a second bone; and
   a plurality of second bearing components, each of the second bearing components being configured to be interchangeably coupled to the second stem structure, each of the second bearing components having a bearing surface that is configured to engage the first and second condyle portions, each of the bearing surfaces of the plurality of second bearing components being configured differently from the bearing surfaces of a remaining quantity of the second bearing components, each of the bearing surfaces providing a varying degree of constraint between the first and second stem structures as the first and second stem structures are rotated relative to one another;
   wherein each of the plurality of second bearing components defines a first bearing face opposed to a second bearing face, the first condyle portion bears on the first bearing face and the second condyle portion bears on the second bearing face, the first condyle portion and the second condyle portion are both exterior to the second bearing component, the first bearing face defines both a first bearing surface and a second bearing surface and the second bearing face defines both a third bearing surface and a fourth bearing surface, the first bearing surface and the second bearing surface are defined around respective first and second center axes, the first center axis is formed at an angle relative to the second center axis; and
   wherein each of the second bearing components includes a different angle between the first and second center axes to provide the varying degree of constraint among the plurality of second bearing components.

2. The prosthetic joint kit of claim 1, wherein at least one of the bearing surfaces is configured such that the varying degree of constraint is provided in a direction that is coincident to an axis about which the first and second stem structures rotate relative to one another.

3. The prosthetic joint kit of claim 1, wherein at least one of the bearing surfaces is configured such that the varying degree of constraint is provided in a varus/valgus direction.

4. The prosthetic joint kit of claim 1, wherein at least one of the bearing surfaces is configured such that the varying degree of constraint is provided in both a direction that is coincident to an axis about which the first and second stem structures rotate relative to one another and in a varus/valgus direction.

5. The prosthetic joint kit of claim 1, further comprising a third bearing component that is configured to be substituted for the second bearing components and selectively coupled to the second stem structure, the third bearing component having a third bearing surface that is configured to engage the first and second condyle portions, the third bearing surface being configured so as to provide a constant degree of constraint between the first and second stem structures as the first and second stem structures are rotated relative to one another.

6. The prosthetic joint kit of claim 1 wherein the at least partially spherically shaped first condyle portion is a second bearing surface and the at least partially spherically shaped second condyle portion defines a third bearing surface;
wherein the first bearing component further includes a connection member operable to interconnect the first condyle portion and the second condyle portion substantially at an apex of the at least partially spherically shaped first condyle portion and second condyle portion;
wherein the connection member of the first bearing component is operable to extend through a passage defined by each of the plurality of second bearing components to assist in holding the first bearing component relative to the second bearing component.

7. The prosthetic joint kit of claim 1, further comprising:
a first transition region defined between the first bearing surface and the second bearing surface on the first bearing face; and
a second transition region defined between the third bearing surface and the fourth bearing surface on the second bearing face.

8. The prosthetic joint kit of claim 1, wherein the first stem structure defines a bifurcated third end having a first arm operable to be positioned in a first slotted aperture defined by the first condyle portion and a second arm operable to be positioned a second slotted aperture defined by the second condyle portion;
wherein the first condyle portion and the second condyle portion are fixed relative to the first stem structure.

9. The prosthetic joint kit of claim 8, further comprising:
a first fixation pin; and
a second fixation pin;
wherein the first fixation pin is operable to pass through a pin aperture in the first condyle portion, the slotted aperture in the first condyle portion, and a first arm pin aperture in the first arm of the first stem structure;
wherein the second fixation pin is operable to pass through a second pin aperture in the second condyle portion, the slotted aperture in the second condyle portion, and a second arm pin aperture in the second arm of the first stem structure.

10. A prosthetic joint kit comprising:
a first stem having a first end adapted to fit within a medullary canal of a first bone;
a first bearing component including:
a first dome shaped condyle portion defined by a first arc;
a second dome shaped condyle portion defined by a second arc; and
a connecting member interconnecting the second dome shaped condyle portion and the first dome shaped condyle portion;
a second stem having a second end that is adapted to fit within a medullary canal of a second bone; and
a second bearing component, including:
a first bearing side and a second bearing side, wherein the first bearing side is opposed to the second bearing side;
a first concave bearing surface defined around a first center axis on the first bearing side;
a second concave bearing surface defined around a second center axis on the second bearing side;
each of the first bearing side and the second bearing side is configured to engage one of the first or second dome shaped condyle portions;
a third concave bearing surface defined around a third center axis on the first bearing side, wherein the first center axis of the first concave bearing surface is formed at an angle through the second bearing component relative to the third center axis of the third concave bearing; and
wherein the second concave bearing surface has a fourth concave bearing surface defined around a fourth center axis on the second bearing side, and the second center axis of the second concave bearing surface is formed at an angle through the second bearing component relative to the fourth center axis of the fourth concave bearing surface.

11. The prosthetic joint kit of claim 10, wherein the second bearing component includes a plurality of second bearing components;
wherein each of the plurality of second bearing components has a third or fourth concave bearing surface that is configured differently from a third or fourth concave bearing surface of another of the second bearing components, each of the third or fourth concave bearing surfaces providing a varying degree of constraint between the first and second stems as the first and second stems are rotated relative to one another;
wherein each of the plurality of the second bearing components is configured to be interchangeably coupled to the second stem.

12. The prosthetic joint kit of claim 10, wherein at least one of the concave bearing surfaces is configured such that the varying degree of constraint is provided in a varus/valgus direction.

13. The prosthetic joint kit of claim 10, wherein at least one of the concave bearing surfaces is configured such that the varying degree of constraint is provided in both a direction that is coincident to an axis about which the first and second stem structures rotate relative to one another and in a varus/valgus direction.

14. The prosthetic joint kit of claim 10, further comprising:
a first transition region defined between the first concave bearing surface and the third concave bearing surface on the first bearing side; and
a second transition region defined between the second concave bearing surface and a fourth concave bearing surface on a second bearing side.

* * * * *

UNITED STATES PATENT AND TRADEMARK OFFICE
CERTIFICATE OF CORRECTION

| | |
|---|---|
| PATENT NO. | : 7,625,406 B2 |
| APPLICATION NO. | : 11/780365 |
| DATED | : December 1, 2009 |
| INVENTOR(S) | : Bereisman et al. |

It is certified that error appears in the above-identified patent and that said Letters Patent is hereby corrected as shown below:

| Col. | Line | Claim | |
|---|---|---|---|
| 1 | 42 | | "the type" should be --this type--. |
| 1 | 56 | | Delete "of amount". |
| 2 | 2 | | * "prostheses" should be --prosthesis--. |
| 2 | 8 | | * "a ulnar" should be --an ulnar--. |
| 2 | 14 | | * "need" should be --needs--. |
| 2 | 18 | | After "is", insert --a--. |
| 2 | 33 | | "plurality" should be --modularity-. |
| 2 | 49 | | After "pair", insert --of--. |
| 2 | 53 | | After "further", insert --object--. |
| 3 | 10 | | "preludes" should be --precludes--. |
| 3 | 12 | | After "not", insert --to--. |
| 3 | 27 | | After "with", insert --a--. |
| 3 | 34 | | After "joint", insert --kit--. |
| 3 | 47 | | "of portion" should be --of a portion--. |
| 4 | 1 | | "of portion of" should be --of a portion of a--. |
| 4 | 12 | | After "view", insert --of a--. |
| 4 | 18 | | * "of second" should be --of a second--. |
| 4 | 27 | | After "clip", insert --member--. |
| 4 | 55 | | After "alternative coupling", insert --means for coupling--. |
| 5 | 7 | | "indicted" should be --indicated--. |
| 5 | 12 | | "will be" should be --will not be--. |
| 6 | 10 | | "place" should be --placed--. |

Signed and Sealed this
Seventeenth Day of April, 2012

David J. Kappos
*Director of the United States Patent and Trademark Office*

CERTIFICATE OF CORRECTION (continued)
U.S. Pat. No. 7,625,406 B2

| | | | |
|---|---|---|---|
| 7 | 32 | | * "form" should be --from--. |
| 7 | 35 | | * "form" should be --from--. |
| 8 | 19 | | "is includes" should be --it includes--. |
| 8 | 22 | | "portions" should be --portion--. |
| 8 | 22 | | "purposed" should be --purposes--. |
| 8 | 51 | | * After "relative", delete "to". |
| 9 | 38 | | "third structure" should be --third stem structure--. |
| 9 | 53 | | After "second bearing component", insert --18, a fourth bearing component 222, and a fifth bearing component--. |
| 13 | 40 | | * "FIG. 19d" should be --FIG. 19D--. |
| 13 | 50 | | * "a integrally" should be --an integrally--. |
| 14 | 29 | | "500p'" should be --500'--. |
| 14 | 56 | | "form" should be --from--. |
| 15 | 9 | | "an cam" should be --a cam--. |
| 15 | 14 | | "structure" should be --structures--. |
| 15 | 21 | | "portion a" should be --portion of a--. |
| 16 | 9 | | "720" should be --702--. |
| 16 | 57 | | "cable 810" should be --cables 810--. |
| 17 | 15 | | * "cable 810" should be --cables 810--. |
| 17 | 16 | | "cable 810" should be --cables 810--. |
| 17 | 17 | | "cable 810" should be --cables 810--. |
| 18 | 3 | | "are" should be --art--. |
| 20 | 22 | 10 | After "bearing", insert --surface--. |
| 20 | 59 | 14 | "a fourth" should be --the fourth--. |